US006197505B1

(12) United States Patent
Norberg et al.

(10) Patent No.: US 6,197,505 B1
(45) Date of Patent: Mar. 6, 2001

(54) METHODS FOR ASSESSING CARDIOVASCULAR STATUS AND COMPOSITIONS FOR USE THEREOF

(75) Inventors: Leif Torbjörn Norberg; Maria Kristina Andersson; Per Harry Rutger Lindström, all of Uppsala (SE)

(73) Assignee: Pyrosequencing AB, Uppsala (SE)

( * ) Notice: Subject to any disclaimer, the term of this patent is extended or adjusted under 35 U.S.C. 154(b) by 0 days.

(21) Appl. No.: 09/050,159

(22) Filed: Mar. 27, 1998

Related U.S. Application Data

(60) Provisional application No. 60/042,930, filed on Apr. 4, 1997.

(51) Int. Cl.$^7$ .............................. C12Q 1/68; C12N 9/00; C07H 17/00; A61K 38/00
(52) U.S. Cl. ............................ 435/6; 435/183; 536/23.1; 536/24.31; 530/316
(58) Field of Search ...................... 435/6, 183; 536/23.1, 536/24.31; 530/316

(56) References Cited

U.S. PATENT DOCUMENTS

| | | | |
|---|---|---|---|
| 5,374,525 | * 12/1994 | Lalouel et al. | 435/6 |
| 5,589,584 | 12/1996 | Lalouel et al. | 536/24.31 |
| 5,763,168 | 6/1998 | Lalouel et al. | 436/6 |
| 5,800,990 | 9/1998 | Raynolds et al. | 435/6 |

FOREIGN PATENT DOCUMENTS

| | | |
|---|---|---|
| WO 87 02709 | 5/1987 | (WO) . |
| WO 88 08457 | 11/1988 | (WO) . |
| WO 94 08048 | 4/1994 | (WO) . |
| WO 98 45477 | 10/1998 | (WO) . |
| WO 99 37761 | 7/1999 | (WO) . |

OTHER PUBLICATIONS

Cambien et al., Am. J. Hum. Genet., 1999, 65:183–191.
Hingorani et al., Journal of Hypertension, 1995, 13:1602–1609.
Jeunemaitre et al., Am. J. Hum. Genet., 1997, 60:1448–1460.
Maqbool et al., The Lancet, 1999, 353:897.
Poirier et al., Journal of Hypertension, 1998, 16(10):1443–1447.
Reihsaus et al., Am. J. Respir. Cell Mol. Biol., 1993, 8:334–339.
Rieder et al., Nature Genetics, 1999, 22:59–62.
Soubrier, F., Journal of Hypertension, 1993, 11(suppl 5):S20–S26.
Timmerman et al., Mutation Note #19, 1997, *Novel DNA sequence differences in the beta2–adrenergic receceptor gene promoter region.*
Soubrier et al., Renin–Angiotensin System Genes as Candidate Genes in Cardiovascular Diseases, Trends in Cardiovascular Med., 3:250–258, 1993.
Timmerman et al., Beta–2 Adrenoreceptor genetic variation is associated with genetic predisposition to essential hypertension: The bergen blood pressure study Kidney Intl., 53:1455–1460, 1998.
Brand et al., Structural analysis and evaluation of the aldosterone synthase gene in hypertension, Hypertension, 32:198–204, 1998.
Frossard et al., Correlations between RFLPs on the human renin gene locus and clinical variables of blood pressure regulation, Biogenic Amines, 11:313–324, 1995.
Dudley, C. et al., "Prediction of patient responses to anti–hypertensive drugs using genetic polymorphisms: Investigation of renin–angiotensin system genes", Journal of Hypertension, 1996, 14(2):259–262.
Raynolds et al., The Role of Genetic Variants in Angiotensin I Converting Enzyme, Angiotensinogen and the Angiotensin II type–1 Receptor in the Pathophysiology of Heart Muscle Disease, Eur. Heart J., 1995 Nov; 16 Suppl. K:23–30.
Raynolds et al., The Association Between the Angiotensin I Converting Enzyme Gene Polymorphism and Cardiovascular Disease, Coron. Artery Dis., Apr. 1995; 6(4):302–9.
Abraham et al., Importance of Angiotensin–Converting Enzyme in Pulmonary Hypertension, Cardiology 1995; 86 Suppl.:9–15.
Raynolds et al., Angiotensin–Converting Enzyme DD Genotype in Patients with Ischaemic or Idiopathic Dilated Cardiomyopathy, Lancet 1993, Oct. 30; 342 (8879):1073–5.
Bonnardeaux et al., Angiotensin II Type 1 Receptor Gene Polymorphisms in Human Essential Hypertension, Hypertension, 24:63–69, 1994.
Cambien, et al., Deletion Polymorphism in the Gene for Angiotensin–Converting Enzyme is a Potent Risk Factor for Myocardial Infarction, Nature, 359:41–644, 1992.
Coffman, A Genetic Approach for Studying the Physiology of the Type 1A (AT$_{1A}$) Angiotensin Receptor, Semin. Nephrol., 17:404–411, 1997.
Esther et al., Mice Lacking Angiotensin–Converting Enzyme Have Low Blood Pressure, Renal Pathology, and Reduced Male Fertility, Lab. Invest., 74:953–965, 1996.

(List continued on next page.)

Primary Examiner—Karen Cochrane Carlson
(74) Attorney, Agent, or Firm—Darby & Darby

(57) ABSTRACT

The present invention provides methods for assessing cardiovascular status in an individual, which comprise determining the sequence at one or more polymorphic positions within the human genes encoding angiotensin converting enzyme (ACE), angiotensinogen (AGT), and/or type 1 angiotensin II receptor (AT1). The invention also provides isolated nucleic acids encoding ACE, AGT, and AT1 polymorphisms, nucleic acid probes that hybridize to polymorphic positions, kits for the prediction of cardiovascular status, and nucleic acid and peptide targets for use in identifying candidate cardiovascular drugs.

40 Claims, No Drawings

OTHER PUBLICATIONS

Inuoe et al. A Nucleotide Substitution in the Promoter on Human Angiotensinogen is Associated with Essential Hypertension and Affects Basal Transcription In Vitro, J. Clin. Invest., 99:1786, 1997.

Ishigami et al., Molecular Variant of Angiotensinogen Gene is Associated with Coronary Atherosclerosis, Circulation, 91:951–4, 1995.

Jeunemaitre et al., Molecular Basis of Human Hypertension: Role of Angiotensinogen, Cell, 71:169–180, 1992.

Kamitani et al., Significance of the Angiotensinogen Gene Polymorphism as a Risk Factor for Myocardial Infarction in the Japanese, Hypertension, 24:381, 1994.

Murakami et al., Hypertensive and Hypotensive Mice Produced by the Introduction and Disruption of Genes on the Renin–Angiotensin System, Blood Press. Suppl., 2:36–40, 1996.

Rolfs et al., Genetic Polymorphisms of the Angiotensin II Type 1 ($AT_1$) Receptor Gene, Eur. Heart. J., 15:Suppl. D:108–112, 1994.

Tiret et al., Synergistic Effects of Angiotensin–Converting Enzyme and Angiotensin–II Type 1 Receptor Gene Polymorphisms on Risk of Myocardial Infarction, The Lancet, 344:910–913, 1994.

Villard et al, Identification of New Polymorphisms of the Angiotensin I–Converting Enzyme (ACE) Gene, and Study of Their Relationship to Plasma ACE Levels by Two–QTL Segregation–Linkage Analysis, Am. J. Hum. Genet., 58:1268–1278, 1996.

* cited by examiner

METHODS FOR ASSESSING CARDIOVASCULAR STATUS AND COMPOSITIONS FOR USE THEREOF

This application claims priority under 35 U.S.C. § 119 from provisional U.S. application Ser. No. 60/042,930, filed Apr. 4, 1997.

FIELD OF THE INVENTION

The present invention relates to genetic polymorphisms useful for assessing cardiovascular status in humans.

BACKGROUND OF THE INVENTION

The renin-angiotensin-aldosterone system (RAAS) plays an important role in cardiovascular physiology in mammals. Specifically, RAAS regulates salt-water homeostasis and the maintenance of vascular tone. Stimulation or inhibition of this system raises or lowers blood pressure, respectively, and disturbances in this system may be involved in the etiology of, for example, hypertension, stroke, and myocardial infarction. The RAAS system may also have other functions such as, e.g., control of cell growth. The renin-angiotensin system includes at least renin, angiotensin converting enzyme (ACE), angiotensinogen (AGT), type 1 angiotensin II receptor (AT1), and type 2 angiotensin II receptor (AT2).

AGT is the specific substrate of renin, an aspartyl protease. The human AGT gene contains five exons and four introns which span 13Kb (Gaillard et al., *DNA* 8:87–99, 1989; Fukamizu et al., *J. Biol. Chem.* 265:7576–7582, 1990). The first exon (37 bp) codes for the 5' untranslated region of the mRNA. The second exon codes for the signal peptide and the first 252 amino acids of the mature protein. Exons 3 and 4 are shorter and code for 90 and 48 amino acids, respectively. Exon 5 contains a short coding sequence (62 amino acids) and the 3'-untranslated region.

Plasma AGT is synthesized primarily in the liver and its expression is positively regulated by estrogens, glucocorticoids, thyroid hormones, and angiotensin II (Ang II) (Clauser et al., *Am. J. Hypertension* 2:403–410, 1989). Cleavage of the amino-terminal segment of AGT by renin releases a decapeptide prohormone, angiotensin-I, which is further processed to the active octapeptide angiotensin II by the dipeptidyl carboxypeptidase designated angiotensin-converting enzyme (ACE). Cleavage of AGT by renin is the rate-limiting step in the activation of the renin-angiotensin system.

Several epidemiological observations indicate a possible role of AGT in blood pressure regulation. A highly significant correlation between plasma AGT concentration and blood pressure has been observed in epidemiological studies (Walker et al., *J. Hypertension* 1:287–291, 1979). Interestingly, a number of allelic dimorphisms have been identified in the AGT gene. The frequency of at least two of them (174M and 235T) have been partially characterized and in certain populations shown to be significantly elevated in hypertensive subjects (Jeunemaitre et al., *Cell* 71:169–180, 1992). In addition, a specific polymorphism, 235T, has been suggested to be directly involved in coronary atherosclerosis (Ishigami et al., *Circulation* 91:951–4, 1995). Futhermore, the presence of A or G at position 1218 in the AGT regulatory region has been correlated with differences in in vitro transcriptional capacity for this gene (Inuoe et. al., *J. Clin. Invest.* 99:1786, 1997.

The human ACE gene is also a candidate as a marker for hypertension and myocardial infarction. ACE inhibitors constitute an important and effective therapeutic approach in the control of human hypertension (Sassaho et al. *Am. J. Med.* 83:227–235, 1987). In plasma and on the surface of endothelial cells, ACE converts the inactive angiotensin I molecule (Ang I) into active angiotensin II (Ang II) (Bottari et al., *Front. Neuroendocrinology* 14:123–171, 1993). Another ACE substrate is bradykinin, a potent vasodilator and inhibitor of smooth muscle cell proliferation, which is inactivated by ACE (Ehlers et al., *Biochemistry* 28:5311–5318, 1989; Erdos, E. G., *Hypertension* 16:363–370, 1990; Johnston, C. I. *Drugs* (suppl. 1) 39:21–31, 1990).

Levels of ACE are very stable within individuals, but differ greatly between individuals. Plasma ACE levels have been suggested to be genetically determined as a consequence of diallelic polymorphisms, situated within or close to the ACE gene. Prior to the present invention, no definitive association was demonstrated between polymorphisms and hypertension or blood pressure. However, a greater risk of myocardial infarction has been identified in a group of subjects with an ACE polymorphism designated ACE-DD (Cambien et al., *Nature* 359:641–644, 1992), and a 12-fold greater risk of myocardial infarction has been identified in a subgroup of patients having a combination of the ACE polymorphism ACE-DD and one of the AGT polymorphisms (235T) described above (Kamitani et al., *Hypertension* 24:381, 1994). Recently, six ACE polymorphisms were identified and characterized (Villard et al., *Am. J. Human Genet.* 58:1268–1278, 1996).

The vasoconstrictive, cell growth-promoting and salt conserving actions of Ang II are mediated through binding to and activation of angiotensin receptors, of which at least two types have been cloned (AT1 and AT2). The type 1 Ang II receptor (AT1), a G-protein-coupled seven transmembrane domain protein, is widely distributed in the body and mediates almost all known Ang II effects (Fyhrquist et al., *J. Hum. Hypertension* 5:519–524, 1995).

Several polymorphisms have been identified in the AT1 receptor gene. Initial studies suggest that at least one of them is more frequent in hypertensive subjects (AT$^{1166}$C) (Bonnardeaux et al., *Hypertension* 24:63–69, 1994). This polymorphism, combined with the ACE-DD polymorphism, has been shown to correlate strongly with the risk of myocardial infarction (Tiret et al., *Lancet* 344:910–913, 1994).

The high morbidity and mortality associated with cardiovascular disease demonstrate a need in the art for methods and compositions that allow the determination and/or prediction of the therapeutic regimen that will result in the most positive treatment outcome in a patient suffering from cardiovascular disease. This includes identification of individuals who are more or less susceptible to particular therapeutic regimens, including, e.g., particular drugs that are conventionally used to treat cardiovascular disease. There is also a need in the art for methods and compositions that allow the identification of individuals having a predisposition to cardiovascular disease, such as, e.g., myocardial infarction, hypertension, atherosclerosis, and stroke to facilitate early intervention and disease prevention.

SUMMARY OF THE INVENTION

The present invention provides methods for assessing cardiovascular status in a human individual. Cardiovascular status is the physiological status of the cardiovascular system as reflected in one or more status markers. Status markers include without limitation clinical parameters such as, e.g., blood pressure or electrocardiographic profile, as well as diagnoses of cardiovascular status made by skilled medical practitioners, such as, e.g., acute myocardial infarction, silent myocardial infarction, stroke, and atherosclerosis. Also included in the evaluation of cardiovascular status are changes in status markers with time. The methods of the invention are carried out by the steps of:

(i) determining the sequence of one or more polymorphic positions within one or more of the genes encoding angiotensin converting enzyme (ACE), angiotensinogen (AGT), and type 1 angiotensin II receptor (AT1) in the individual to establish a polymorphic pattern for the individual; and (ii) comparing the polymorphic pattern established in (i) with the polymorphic patterns of individuals exhibiting predetermined markers of cardiovascular status. The polymorphic pattern of the individual is, preferably, highly similar and, most preferably, identical to the polymorphic pattern of individuals who exhibit particular status markers, cardiovascular syndromes, and/or particular patterns of response to therapeutic interventions.

For example, a comparison of the polymorphic pattern of an individual with the polymorphic patterns of individuals exhibiting differing responses to a particular therapeutic intervention can be used to predict the degree of responsivity of the individual to such intervention. In a similar manner, the methods of the invention can be used to predict predisposition to different cardiovascular syndromes.

The invention also provides isolated nucleic acids encoding ACE, AGT, and AT1 in an individual, each of which comprises at least one polymorphic position. In preferred embodiments, the polymorphic position, either alone or in combination with other polymorphic positions in the sequence of human ACE, AGT, or AT1, or in one or more other human genes, is predictive of a particular level of responsivity to a given treatment and/or indicates a predisposition to one or more clinical syndromes associated with cardiovascular disease.

The isolated nucleic acids according to the invention (which are described using the numbering indicated in Table 1 below) include without limitation:

(i) Nucleic acids encoding ACE having one or more polymorphic positions at the position in the regulatory region (SEQ ID NO: 129) numbered 5106; positions in the coding region (SEQ ID NO: 130) numbered 375, 582, 731, 1060, 2741, 3132, 3387, 3503, and 3906; and position 1451 as numbered in Genbank entry X62855 (SEQ ID NO: 128). In preferred embodiments, the sequences at the polymorphic positions in the ACE regulatory region are one or more of 5106C and 5106T; and the sequences at the polymorphic positions in the coding region are one or more of 375A, 375C, 582C, 582T, 731A, 731G, 1060G, 1060A, 2741G, 2741T, 3132C, 3132T, 3387T, 3387C, 3503G, 3503C, 3906G, and 3906A. The invention also encompasses a nucleic acid encoding a deletion of nucleotides 1451–1783 as numbered in Genbank entry X62855.

(ii) Nucleic acids encoding AGT having one or more polymorphic positions at positions in the regulatory region (SEQ ID NO: 123) numbered 395, 412, 432, 449, 692, 839, 1007, 1072, and 1204; positions in the coding region (SEQ ID NO: 124–127) numbered 273, 912, 997, 1116, and 1174; and position 49 as numbered in Genbank entry M24688 (SEQ ID NO: 126). In preferred embodiments, the sequences at the polymorphic positions in the AGT regulatory region are one or more of 395T, 395A, 412C, 412T, 432G, 432A, 449T, 449C, 692C, 692T, 839G, 839A, 1007G, 1007A, 1072G, 1072A, 1204C, and 1204A; the sequences at the polymorphic position in the coding region are one or more of 273C, 273T, 912C, 912T, 997G, 997C, 1116G, 1116A, 1174C and 1174A; and the sequence at position 49 in Genbank entry M24688 is either A or G.

(iii) Nucleic acids encoding AT1 having one or more polymorphic positions at positions in the regulatory region (SEQ ID NO: 131) numbered 1427, 1756, 1853, 2046, 2354, 2355, and 2415; and the position in the coding region (SEQ ID NO: 132–133 which are contiguous) numbered 449. In preferred embodiments, the sequences at the polymorphic positions in the AT1 regulatory region are one or more of 1427A, 1427T, 1756T, 1756A, 1853T, 1853G, 2046T, 2046C, 2354A, 2354C, 2355G, 2355C, 2415A and 2415G; and the sequences at the polymorphic positions in the coding region are one or more of 449G, 449C, 678T, 678C, 1167A, 1167G, 1271A, and 1271C.

The invention also encompasses libraries of isolated nucleic acid sequences, wherein each sequence in the library comprises one or more polymorphic positions in the genes encoding human ACE, AGT, or AT1, including without limitation the polymorphic positions and sequences disclosed herein. Also provided are nucleic acid probes that hybridize specifically to the identified poliymorphic positions; peptides and polypeptides comprising polymorphic positions; and polymorphism-specific antibodies, i.e., sequence-specific antibodies that bind differentially to polymorphic variants of ACE, AGT, or AT1 polypeptides and, preferably, can be used to identify particular polymorphic variants.

In yet another aspect, the invention provides kits for the determination of polymorphic patterns in an individual's ACE, AGT, and/or AT1 genes. The kits comprise a means for detecting polymorphic sequences, including without limitation oligonucleotide probes that hybridize at or adjacent to the polymorphic positions and polymorphism-specific antibodies.

In yet another aspect, the invention provides nucleic acid and polypeptide targets for use in screening methods to identify candidate cardiovascular drugs. Nucleic acid targets may be, e.g., DNA or RNA and are preferably at least about 10, and most preferably at least about 15, residues in length and comprise one or more polymorphic positions. Peptide targets are at least about 5 amino acids in length and may be as large or larger than full-length ACE, AGT, or AT1 polypeptides.

DETAILED DESCRIPTION OF THE INVENTION

All patents, patent applications, publications and other materials cited herein are hereby incorporated by reference in their entirety. In the case of inconsistencies, the present description, including definitions, is intended to control.

Definitions:

1. A "polymorphism" as used herein denotes a variation in the sequence of a gene in an individual. A "polymorphic position" is a predetermined nucleotide position within the sequence of a gene or a predetermined amino acid position in the sequence of a polypeptide at which a polymorphism is located. An individual "homozygous" for a particular polymorphism is one in which both copies of the gene contain the same sequence at the polymorphic position. An individual "heterozygous" for a particular polymorphism is one in which the two copies of the gene contain different sequences at the polymorphic position.

2. A "polymorphism pattern" as used herein denotes a set of one or more polymorphisms, which may be contained in the sequence of a single gene or a plurality of genes. A polymorphism pattern may comprise nucleotide or amino acid polymorphisms.

3. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. Nucleic acids include without limitation single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

4. An "isolated" nucleic acid or polypeptide as used herein refers to a nucleic acid or polypeptide that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

5. A nucleic acid or polypeptide sequence that is "derived from" a designated sequence refers to a sequence that corresponds to a region of the designated sequence. For nucleic acid sequences, this encompasses sequences that are homologous or complementary to the sequence.

6. A "probe" refers to a nucleic acid or oligonucleotide that forms a hybrid structure with a sequence in a target nucleic acid due to complementarity of at least one sequence in the probe with a sequence in the target nucleic acid.

7. Nucleic acids are "hybridizable" to each other when at least one strand of nucleic acid can anneal to another nucleic acid strand under defined stringency conditions.

Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art. For example, "high stringency" as used herein refers to hybridization and/or washing at 68° C. in 0.2XSSC, at 42° C. in 50% formamide, 4XSSC, or under conditions that afford levels of hybridization equivalent to those observed under either of these two conditions.

8. A "gene" for a particular protein as used herein refers to a contiguous nucleic acid sequence corresponding to a sequence present in a genome which comprises (i) a "coding region," which comprises exons (i.e., sequences encoding a polypeptide sequence or "protein-coding sequences"), introns, and sequences at the junction between exons and introns; and (ii) regulatory sequences, which flank the coding region at both 5' and 3' termini. For example, the "ACE gene" as used herein encompasses the regulatory and coding regions of the human gene encoding angiotensin converting enzyme. Similarly, the "AGT gene" encompasses regulatory and coding regions of the human gene encoding angiotensinogen and the "AT1 gene" encompasses regulatory and coding regions of the human gene encoding type I angiotensin II receptor. Typically, regulatory sequences according to the invention are located 5' (i.e., upstream) of the coding region segment. The reference sequences, obtained from Genbank, which were used in practicing the present invention are shown in Table 1.

TABLE 1

| Abbreviation | Compared master sequence | Numbering according to sequence entry in GenBank |
| --- | --- | --- |
| AGT Regulatory Region | X15323 | X15323 (SEQ ID NO:123) |
| AGT Coding Region | M24686 (exon 2) (SEQ ID NO: 124) M24687 (exon 3) (SEQ ID NO: 125) M24688 (exon 4) (SEQ ID NO: 126) M24689 (exon 5) (SEQ ID NO: 127) | Protein-coding sequences from exon 2–5 were spliced together as described in the GenBank entries. Nucleotide 1 is assigned to the first nucleotide of the initiator methionine codon. |
| | X62855 (intron 16) (SEQ ID NO: 128) | X62855 |
| ACE Regulatory Region | X94359 (SEQ ID NO: 129) | X94359 |
| ACE Coding Region | J04144 (SEQ ID NO: 130) | J04144 Nucleotide 1 is assigned to the first nucleotide of the initiator methionine codon. |
| AT1 Regulatory Region | U07144 (SEQ ID NO: 131) | U07144 |
| AT1 Coding Region | S80239 (exon 3) (SEQ ID NO: 132) S77410 (exon 5) (SEQ ID NO: 133) | The protein-coding sequence of S80239 was spliced to position 288 of entry S77410. Nucleotide 1 is assigned to the first nucleotide of the initiator methionine codon in entry S80239. |

The present inventors have surprisingly and unexpectedly discovered the existence of genetic polymorphisms within the human genes encoding ACE, AGT, and AT1 which, singly or in combination, can be used to assess cardiovascular status. In accordance with the invention, the polymorphic pattern of ACE, AGT, and/or AT1 sequences in an individual can predict the responsivity of the individual to particular therapeutic interventions and serve as an indicator of predisposition to various forms of cardiovascular disease. The invention provides methods for assessing cardiovascular status by detecting polymorphic patterns in an individual. The present invention also provides isolated nucleic acids derived from the ACE, AGT, and AT1 genes which comprise these polymorphisms, including probes which hybridize specifically to polymorphic positions; isolated polypeptides and peptides comprising polymorphic residues; and antibodies which specifically recognize ACE, AGT, or AT1 polypeptides containing one or more polymorphic amino acids.

Methods for Assessing Cardiovascular Status

The present invention provides diagnostic methods for assessing cardiovascular status in a human individual. Cardiovascular status as used herein refers to the physiological status of an individual's cardiovascular system as reflected in one or more markers or indicators. Status markers include without limitation clinical measurements such as, e.g., blood pressure, electrocardiographic profile, and differentiated blood flow analysis. Status markers according to the invention include diagnoses of one or more cardiovascular syndromes, such as, e.g., hypertension, acute myocardial infarction, silent myocardial infarction, stroke, and atherosclerosis. It will be understood that a diagnosis of a cardiovascular syndrome made by a medical practitioner encompasses clinical measurements and medical judgement. Status markers according to the invention are assessed using conventional methods well known in the art. Also included in the evaluation of cardiovascular status are quantitative or qualitative changes in status markers with time, such as would be used, e.g., in the determination of an individual's response to a particular therapeutic regimen.

The methods are carried out by the steps of:
(i) determining the sequence of one or more polymorphic positions within one or more of the genes encoding angiotensin coverting enzyme (ACE), angiotensinogen (AGT), or type 1 angiotensin II receptor (AT1) in the individual to establish a polymorphic pattern for the individual; and
(ii) comparing the polymorphic pattern established in (i) with the polymorphic patterns of humans exhibiting different markers of cardiovascular status. The polymorphic pattern of the individual is, preferably, highly similar and, most preferably, identical to the polymorphic pattern of individuals who exhibit particular status markers, cardiovascular syndromes, and/or particular patterns of response to therapeutic interventions. Polymorphic patterns may also include polymorphic positions in other genes which are shown, in combination with one or more polymorphic positions in ACE, AGT, or AT1, to correlate with the presence of particular status markers. In one embodiment, the method involves comparing an individual's polymorphic pattern with polymorphic patterns of individuals who have been shown to respond positively or negatively to a particular therapeutic regimen. Therapeutic regimen as used herein refers to treatments aimed at the elimination or amelioration of symptoms and events associated cardiovascular disease. Such treatments include without limitation one or more of alteration in diet, lifestyle, and exercise regimen; invasive and noninvasive surgical techniques such as atherectomy, angioplasty, and coronary bypass surgery; and pharmaceutical interventions, such as administration of ACE inhibitors, angiotensin II receptor antagonists, diuretics, alpha-adrenoreceptor antagonists, cardiac glycosides, phosphodiesterase inhibitors, beta-adrenoreceptor antagonists, calcium channel blockers, HMG-CoA reductase inhibitors, imidazoline receptor blockers, endothelin receptor blockers, and organic nitrites. Interventions with pharmaceutical agents not yet known whose activity correlates with particular polymorphic patterns associated with cardiovascular disease are also encompassed. The present inventors have discovered that particular polymorphic patterns correlate with an individual's responsivity to ACE inhibitors (see, e.g., Example 3 below). It is contemplated, for example, that patients who are candidates for a particular therapeutic regimen will be screened for polymorphic patterns that correlate with responsivity to that particular regimen.

In a preferred embodiment, the presence or absence in an individual of a polymorphic pattern comprising ACE 2193 A/G, AGR 1072 G/A, and ATi 1167 A/G (see below) is determined to identify an individual's responsivity to ACE inhibitors.

In another embodiment, the method involves comparing an individual's polymorphic pattern with polymorphic patterns of individuals who exhibit or have exhibited one or more markers of cardiovascular disease, such as, e.g., high blood pressure, abnormal electrocardiographic profile, myocardial infarction, stroke, or atherosclerosis (see, e.g., Example 2 below).

In practicing the methods of the invention, an individual's polymorphic pattern can be established by obtaining DNA from the individual and determining the sequence at predetermined polymorphic positions in ACE, AGT, and AT1 such as those described above.

The DNA may be obtained from any cell source. Non-limiting examples of cell sources available in clinical practice include blood cells, buccal cells, cervicovaginal cells, epithelial cells from urine, fetal cells, or any cells present in tissue obtained by biopsy. Cells may also be obtained from body fluids, including without limitation blood, saliva, sweat, urine, cerebrospinal fluid, feces, and tissue exudates at the site of infection or inflammation. DNA is extracted from the cell source or body fluid using any of the numerous methods that are standard in the art. It will be understood that the particular method used to extract DNA will depend on the nature of the source.

Determination of the sequence of the extracted DNA at polymorphic positions in ACE, AGT, and/or AT1 genes is achieved by any means known in the art, including but not limited to direct sequencing, hybridization with allele-specific oligonucleotides, allele-specific PCR, ligase-PCR, HOT cleavage, denaturing gradient gel electrophoresis (DDGE), and single-stranded conformational polymorphism (SSCP). Direct sequencing may be accomplished by any method, including without limitation chemical sequencing, using the Maxam-Gilbert method; by enzymatic sequencing, using the Sanger method; mass spectrometry sequencing; and sequencing using a chip-based technology. See, e.g., Little et al., *Genet. Anal.* 6:151, 1996. Preferably, DNA from a subject is first subjected to amplification by polymerase chain reaction (PCR) using specific amplification primers.

In an alternate embodiment, biopsy tissue is obtained from a subject. Antibodies that are capable of distinguishing between different polymorphic forms ACE, AGT, and/or AT1 are then applied to samples of the tissue to determine the presence or absence of a polymorphic form specified by the antibody. The antibodies may be polyclonal or monoclonal, preferably monoclonal. Measurement of specific antibody binding to cells may be accomplished by any known method e.g. quantitative flow cytometry, or enzyme-linked or fluorescence-linked immunoassay. The presence or absence of a particular polymorphism or polymorphic pattern, and its allelic distribution (i.e., homozygosity vs. heterozygosity) is determined by comparing the values obtained from a patient with norms established from populations of patients having known polymorphic patterns.

In an alternate embodiment, RNA is isolated from biopsy tissue using standard methods well known to those of ordinary skill in the art such as guanidium thiocyanate-phenol-chloroform extraction (Chomocyznski et al., 1987, *Anal. Biochem.*, 162:156.) The isolated RNA is then subjected to coupled reverse transcription and amplification by polymerase chain reaction (RT-PCR), using specific oligonucleotide primers. Conditions for primer annealing are chosen to ensure specific reverse transcription and amplification; thus, the appearance of an amplification product is diagnostic of the presence of particular alleles. In another embodiment, RNA is reverse-transcribed and amplified, after which the amplified sequences are identified by, e.g., direct sequencing.

In practicing the present invention, the distribution of polymorphic patterns in a large number of individuals exhibiting particular markers of cardiovascular status is determined by any of the methods described above, and compared with the distribution of polymorphic patterns in patients that have been matched for age, ethnic origin, and/or any other statistically or medically relevant parameters, who exhibit quantitatively or qualitatively different status markers. Correlations are achieved using any method known in the art, including nominal logistic regression or standard least squares regression analysis. In this manner, it is possible to establish statistically significant correlations between particular polymorphic patterns and particular cardiovascular statuses. It is further possible to establish statistically significant correlations between particular polymorphic patterns and changes in cardiovascular status such as, would result, e.g., from particular treatment regimens. In this manner, it is possible to correlate polymorphic patterns with responsivity to particular treatments.

Polymorphic Positions in Genes Encoding ACE, AGT, and AT1

Polymorphic positions in the genes encoding ACE, AGT, and AT1 which are encompassed by the invention are identified by determining the DNA sequence of all or part of the ACE, AGT, and/or AT1 genes in a multiplicity of individuals in a population. DNA sequence determination may be achieved using any conventional method, including, e.g., chemical or enzymatic sequencing.

The polymorphic positions of the invention include without limitation those listed below, whose numbering corresponds to the Genbank sequences listed in Table 1.

(i) ACE: positions in the regulatory region (designated ACR) numbered 5106, 5349, and 5496; positions in the coding region (designated ACE) numbered 375, 582, 731, 1060, 1215, 2193, 2328, 2741, 3132, 3387, 3503, and 3906; and position 1451 as numbered in Genbank entry X62855.

(ii) AGT: positions in the regulatory region (designated AGR) numbered 395, 412, 432, 449, 692, 839, 1007, 1072, 1204, and 1218; positions in the coding region (designated AGT) numbered 273, 620, 803, 912, 997, 1116, and 1174; and position 49 as numbered in Genbank entry M24688.

(iii) AT1: positions in the regulatory region (designated ATR) numbered 1427, 1756, 1853, 2046, 2354, 2355, and 2415; and positions in the coding region (designated AT1) numbered 449, 678, 1167, and 1271.

In preferred embodiments, the sequence at each of the above polymorphic positions is one of:

(i) ACE Regulatory Region: 5106C, 5106T, 5349A, 5349T, 5496T, and 5496C;

(ii) ACE Coding Region: 375A, 375C, 582C, 582T, 731A, 731G, 1060G, 1060A, 1215C, 1215T, 2193G, 2193A, 2328A, 2328G, 2741G, 2741T, 3132C, 3132T, 3387T, 3387C, 3503G, 3503C, 3906G, and 3906A; and a deletion of nucleotides 1451–1783 as numbered in Genbank entry X62855;

(iii) AGT Regulatory Region: 395T, 395A, 412C, 412T, 432G, 432A, 449T, 449C, 692C, 692T, 839G, 839A, 1007G, 1007A, 1072G, 1072A, 1204C, 1204A, 1218A, 1218G;

(iv) AGT Coding Region: 273C, 273T, 620C, 620T, 803T, 803C, 912C, 912T, 997G, 997C, 1116G, 1116A, 1174C, and 1174A; and A or G at position 49 in Genbank entry M24688;

(v) AT1 Regulatory Region: 1427A, 1427T, 1756T, 1756A, 1853T, 1853G, 2046T, 2046C, 2354A, 2354C, 2355G, 2355C, 2415A and 2415G; and (vi) AT1 Coding Region: 449G6 449C, 678T, 678C, 1167A, 1167G, 1271A, and 1271C.

An individual may be homozygous or heterozygous for a particular polymorphic position (see, e.g., Table 6 below).

Non-limiting examples of polymorphic patterns comprising one or more polymorphism in ACE, AGT, and/or AT1 genes according to the invention include the following, which were correlated with an increased incidence of clinical signs of cardiovascular disease:

ACR 5349 A/T, AGR 1218 A; ACR 5496 C, AGR 1204 A/C; ACR 5496 C/T, AGR 1218 A, AGT 620 C/T; ACE 2193 A, AGR 1204 C, ACE 2328 G; ACE 2193 A, AGR 1204 A/C; ACE 3387 T, AGR 1218 A; ACE 3387 T, AGT 620 C/T; AGR 1204 A/C, AT1 678 C/T; AGR 1204 A/C, AT1 1271 A/C; ACE 1215 C, AGR 1204 A/C; AGR 1204 A/C, AT1 1167 A, ACE 3906 A/G; AGR 1204 A, AGT 620 C, AT1 1271 A, AT1 1167 A, AGR 395 A/T; AGR 1204 A/C, AGT 620 C/T, AT1 1271 A/C, AT1 1167 A, AGR 395 T; AGR 1204 A/C, AGT 620 C/T, AT1 1271 A/C, AF1 1167 A/G, AGR 395 T; AGR 1204 A, AT1 678 C, AT1 1167 A, AGR 395 A/T; AGR 1204 A/C, AT1 678 C/T, AT1 1167 A, AGR 395 T; AGT 620 C/T, AT1 1271 A/C, AT1 1167 A, AGR 395 T; AGT 620 C/T, AT1 1271 A/C, AT1 1167 A/G, AGR 395 T; AGT 620 C, AT1 1271 A, AT1 1167 A, AGR 395 A/T; AGT 620 C, AT1 678 A, AT1 1167 A, AGR 395 A/T; AGT 620 C/T, AT1 678 C/T; AT1 1167 A, AGR 395 T; ACE 2193 A, AGR 1218 A, AGT 803 A; ACE 2193 A, AGT 620 C/T; ACE 2328 G, AGT 620 C/T; ACE 3387 T, AGR 1204 A/C; ACE 2193 A, ACE 2328 G, AGR 1204 C; and ACE 2193 A/G, AGR 1072 G/A, AT1 1167 A/G.

Isolated Polymorphic Nucleic Acids, Probes, and Vectors

The present invention provides isolated nucleic acids comprising the polymorphic positions described above for the human ACE, AGT, and AT1 genes; vectors comprising the nucleic acids; and transformed host cells comprising the vectors. The invention also provides probes which are useful for detecting these polymorphisms.

In practicing the present invention, many conventional techniques in molecular biology, microbiology, and recombinant DNA, are used. Such techniques are well known and are explained fully in, for example, Sambrook et al., 1989, *Molecular Cloning: A Laboratory Manual*, Second Edition, Cold Spring Harbor Laboratory Press, Cold Spring Harbor, New York; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); Ausubel et al., *Current Protocols in Molecular Biology*, 1997, (John Wiley and Sons); and *Methods in Enzymology* Vol. 154 and Vol. 155 (Wu and Grossman, and Wu, eds., respectively).

Insertion of nucleic acids (typically DNAs) comprising the sequences of the present invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

The nucleic acids may be isolated directly from cells or may be chemically synthesized using known methods. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by native ACE, AGT, or AT1 gene sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed ACE, AGT, and AT1-derived gene sequences or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression. Non-limiting examples of suitable vectors include without limitation pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Suitable host cells may be transformed/transfected/infected as appropriate by any suitable method including electroporation, $CaCl_2$ mediated DNA uptake, fungal or viral infection, microinjection, microprojectile, or other established methods. Appropriate host cells included bacteria, archebacteria, fungi, especially yeast, and plant and animal cells, especially mammalian cells. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced ACE-, AGT-, or AT1-derived peptides and polypeptides. Nucleic acids encoding ACE-, AGT-, or AT1-derived gene sequences may also be introduced into cells by recombination events. For example, such a sequence can be introduced into a cell and thereby effect homologous recombination at the site of an endogenous gene or a sequence with substantial identity to the gene. Other recombination-based methods such as non-homologous recombinations or deletion of endogenous genes by homologous recombination may also be used.

The nucleic acids of the present invention find use as probes for the detection of genetic polymorphisms and as templates for the recombinant production of normal or variant ACE-, AGT-, or AT1-derived peptides or polypeptides.

Probes in accordance with the present invention comprise without limitation isolated nucleic acids of about 10–100 bp, preferably 15–75 bp and most preferably 17–25 bp in length, which hybridize at high stringency to one or more of the ACE, AGT, or AT1 gene-derived polymorphic sequences disclosed herein or to a sequence immediately adjacent to a polymorphic position. Furthermore, in some embodiments a full-length gene sequence may be used as a probe. In one series of embodiments, the probes span the polymorphic positions in the ACE, AGT, or AT1 genes disclosed above. In another series of embodiments, the probes correspond to sequences immediately adjacent to the polymorphic positions.

Polymorphic ACE, AGT, and AT1 Polypeptides and Polymorphism-Specific Antibodies

The present invention encompasses isolated peptides and polypeptides encoding ACE, AGT, and AT1 comprising polymorphic positions disclosed above. In one preferred embodiment, the peptides and polypeptides are useful screening targets to identify cardiovascular drugs. In another preferred embodiments, the peptides and polypeptides are capable of eliciting antibodies in a suitable host animal that react specifically with a polypeptide comprising the polymorphic position and distinguish it from other polypeptides having a different sequence at that position.

Polypeptides according to the invention are preferably at least five or more residues in length, preferably at least fifteen residues. Methods for obtaining these polypeptides are described below. Many conventional techniques in protein biochemistry and immunology are used. Such techniques are well known and are explained in *Immunochemical Methods in Cell and Molecular Biology,* 1987 (Mayer and Waler, eds; Academic Press, London); Scopes, 1987, *Protein Purification: Principles and Practice,* Second Edition (Springer-Verlag, N.Y.) and *Handbook of Experimental Immunology,* 1986, Volumes I–IV (Weir and Blackwell eds.).

Nucleic acids comprising protein-coding sequences can be used to direct the ITT recombinant expression of ACE-, AGT, or AT1-derived polypeptides in intact cells or in cell-free translation systems. The known genetic code, tailored if desired for more efficient expression in a given host organism, can be used to synthesize oligonucleotides encoding the desired amino acid sequences. The polypeptides may be isolated from human cells, or from heterologous organisms or cells (including, but not limited to, bacteria, fungi, insect, plant, and mammalian cells) into which an appropriate protein-coding sequence has been introduced and expressed. Furthermore, the polypeptides may be part of recombinant fusion proteins.

Peptides and polypeptides may be chemically synthesized by commercially available automated procedures, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against ACE, AGT, or AT1, or against peptides derived therefrom, can be used as purification reagents. Other purification methods are possible.

The present invention also encompasses derivatives and homologues of the polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention also encompasses antibodies that specifically recognize the polymorphic positions of the invention and distinguish a peptide or polypeptide containing a particular polymorphism from one that contains a different sequence at that position. Such polymorphic position-specific antibodies according to the present invention include polyclonal and monoclonal antibodies. The antibodies may be elicited in an animal host by immunization with ACE, AGT, or AT1-derived immunogenic components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well-known in the art and are discussed in more detail below. For example, techniques for producing and processing polyclonal antisera are disclosed in Mayer and Walker, 1987, *Immunochemical Methods in Cell and Molecular Biology*, (Academic Press, London). The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., Schreier et al., 1980, *Hybridoma Techniques;* U.S. Pat. Nos. 4,341,761; 4,399,121; 4,427,783; 4,444,887; 4,466,917; 4,472,500; 4,491,632; and 4,493,890. Panels of monoclonal antibodies produced against ACE, AGT, or AT1-derived epitopes can be screened for various properties; i.e. for isotype, epitope affinity, etc.

The antibodies of this invention can be purified by standard methods, including but not limited to preparative disc-gel electrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification,* 1989, Amicon Division, W. R. Grace & Co. General protein purification methods are described in *Protein Purification: Principles and Practice,* R. K. Scopes, Ed., 1987, Springer-Verlag, New York, N.Y.

Methods for determining the immunogenic capability of the disclosed sequences and the characteristics of the resulting sequence-specific antibodies and immune cells are well-known in the art. For example, antibodies elicited in response to a peptide comprising a particular polymorphic sequence can be tested for their ability to specifically recognize that polymorphic sequence, i.e., to bind differentially to a peptide or polypeptide comprising the polymorphic sequence and thus distinguish it from a similar peptide or polypeptide containing a different sequence at the same position.

Diagnostic Methods and Kits

The present invention provides kits for the determination of the sequence at polymorphic positions within the ACE, AGT, and AT1 genes in an individual. The kits comprise a means for determining the sequence at one or more polymorphic positions, and may optionally include data for analysis of polymorphic patterns. The means for sequence determination may comprise suitable nucleic acid-based and immunological reagents (see below). Preferably, the kits also comprise suitable buffers, control reagents where appropriate, and directions for determining the sequence at a polymorphic position. The kits may also comprise data for correlation of particular polymorphic patterns with desirable treatment regimens or other indicators.

Nucleic-acid-based diagnostic methods and kits:

The invention provides nucleic acid-based methods for detecting polymorphic patterns in a biological sample. The sequence at particular polymorphic positions in the genes encoding ACE, AGT, and/or AT1 is determined using any suitable means known in the art, including without limitation hybridization with polymorphism-specific probes and direct sequencing.

The present invention also provides kits suitable for nucleic acid-based diagnostic applications. In one embodiment, diagnostic kits include the following components:

(i) Probe DNA: The probe DNA may be pre-labelled; alternatively, the probe DNA may be unlabelled and the ingredients for labelling may be included in the kit in separate containers; and (ii) Hybridization reagents: The kit may also contain other suitably packaged reagents and materials needed for the particular hybridization protocol, including solid-phase matrices, if applicable, and standards.

In another embodiment, diagnostic kits include:

(i) Sequence determination primers: Sequencing primers may be pre-labelled or may contain an affinity purification or attachment moiety; and (ii) Sequence determination reagents: The kit may also contain other suitably packaged reagents and materials needed for the particular sequencing protocol. In one preferred embodiment, the kit comprises a panel of sequencing primers, whose sequences correspond to sequences adjacent to the following polymorphic positions: ACE 2193 A/G, AGR 1072 G/A, AT1 1167 A/G; as well as a means for detecting the presence of each polymorphic sequence.

Antibody-based diagnostic methods and kits:

The invention also provides antibody-based methods for detecting polymorphic patterns in a biological sample. The methods comprise the steps of: (i) contacting a sample with one or more antibody preparations, wherein each of the antibody preparations is specific for a particular polymorphic form of either ACE, AGT, or AT1, under conditions in which a stable antigen-antibody complex can form between the antibody and antigenic components in the sample; and (ii) detecting any antigen-antibody complex formed in step (i) using any suitable means known in the art, wherein the detection of a complex indicates the presence of the particular polymorphic form in the sample.

Typically, immunoassays use either a labelled antibody or a labelled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labelled immunoassays, such as ELISA assays.

The present invention also provides kits suitable for antibody-based diagnostic applications. Diagnostic kits typically include one or more of the following components:

(i) Polymorphism-specific antibodies. The antibodies may be pre-labelled; alternatively, the antibody may be unlabelled and the ingredients for labelling may be included in the kit in separate containers, or a secondary, labelled antibody is provided; and (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Drug Targets and Screening Methods

According to the present invention, nucleotide sequences derived from genes encoding ACE, AGT, and AT1 and peptide sequences derived from ACE, AGT, and AT1 polypeptides, particularly those that contain one or more polymorphic sequences, comprise useful targets to identify cardiovascular drugs, i.e., compounds that are effective in treating one or more clinical symptoms of cardiovascular disease.

Drug targets include without limitation (i) isolated nucleic acids derived from the genes encoding ACE, AGT, and AT1, and (ii) isolated peptides and polypeptides derived from ACE, AGT, and AT1 polypeptides, each of which comprises one or more polymorphic positions.

In vitro screening methods:

In one series of embodiments, an isolated nucleic acid comprising one or more polymorphic positions is tested in vitro for its ability to bind test compounds in a sequence-specific manner. The methods comprise:

(i) providing a first nucleic acid containing a particular sequence at a polymorphic position and a second nucleic acid whose sequence is identical to that of the first nucleic acid except for a different sequence at the same polymorphic position;

(ii) contacting the nucleic acids with a multiplicity of test compounds under conditions appropriate for binding; and (iii) identifying those compounds that bind selectively to either the first or second nucleic acid sequence.

Selective binding as used herein refers to any measurable difference in any parameter of binding, such as, e.g., binding affinity, binding capacity, etc.

In another series of embodiments, an isolated peptide or polypeptide comprising one or more polymorphic positions is tested in vitro for its ability to bind test compounds in a sequence-specific manner. The screening methods involve:

(i) providing a first peptide or polypeptide containing a particular sequence at a polymorphic position and a second peptide or polypeptide whose sequence is identical to the first peptide or polypeptide except for a different sequence at the same polymorphic position;

(ii) contacting the polypeptides with a multiplicity of test compounds under conditions appropriate for binding; and (iii) identifying those compounds that bind selectively to one of the nucleic acid sequences.

In preferred embodiments, high-throughput screening protocols are used to survey a large number of test compounds for their ability to bind the genes or peptides disclosed above in a sequence-specific manner.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means.

In vivo screening methods:

Intact cells or whole animals expressing polymorphic variants of genes encoding ACE, AGT, and/or AT1 can be used in screening methods to identify candidate cardiovascular drugs.

In one series of embodiments, a permanent cell line is established from an individual exhibiting a particular polymorphic pattern. Alternatively, cells (including without limitation mammalian, insect, yeast, or bacterial cells) are programmed to express a gene comprising one or more polymorphic sequences by introduction of appropriate DNA. Identification of candidate compounds can be achieved using any suitable assay, including without limitation (i) assays that measure selective binding of test compounds to particular polymorphic variants of ACE, AGT, or AT1; (ii) assays that measure the ability of a test compound to modify (i.e., inhibit or enhance) a measurable activity or function of ACE, AGT, or AT1; and (iii) assays that measure the ability of a compound to modify (i.e., inhibit or enhance) the transcriptional activity of sequences derived from the promoter (i.e., regulatory) regions of ACE, AGT, or AT1 genes.

In another series of embodiments, transgenic animals are created in which (i) one or more human ACE, AGT, or AT1 genes having different sequences at particular polymorphic positions are stably inserted into the genome of the transgenic animal; and/or (ii) the endogenous ACE, AGT, and/or AT1 genes are inactivated and replaced with human ACE, AGT, and/or AT1 genes having different sequences at particular polymorphic positions. See, e.g., Coffman, *Semin. Nephrol.* 17:404, 1997; Esther et al., *Lab. Invest.* 74:953, 1996; Murakami et al., *Blood Press. Suppl.* 2:36, 1996. Such animals can be treated with candidate compounds and monitored for one or more clinical markers of cardiovascular status.

The following are intended as non-limiting examples of the invention.

EXAMPLE 1
Methods for Identification of Polymorphic Positions in Human Genes Encoding ACE, AGT, and AK1

The following studies were performed to identify polymorphic residues within the genes encoding human ACE, AGT, and AT1.

DNA samples were obtained from 277 individuals. The individuals were Caucasian males born in Uppsala, Sweden between 1920 and 1924. Individuals were selected for the test population based on their medical history, i.e., they were either (i) healthy, with no signs of cardiovascular disease (100); or (ii) had suffered one of acute myocardial infarction (68), silent myocardial infarction (34), stroke (18), stroke and acute myocardial infarction (19), or high blood pressure at age 50 (39). DNA samples were obtained from each individual.

DNA sequence analysis was carried out by: (i) amplifying short fragments of each of the ACE, AGT, and AT1 genes using polymerase chain reaction (PCR) and (ii) sequencing the amplified fragments. The sequences obtained from each individual were then compared with known ACE, AGT, and AT1 genomic sequences (see Table 1).

(i) Amplification: PCR reactions employed the primers shown in Table 2 below.

TABLE 2

| Name | Sequence | | Modification *) | Nucleotides | Numbering according to **) |
|---|---|---|---|---|---|
| ACE/79RB | 5'-TGCGTGCTTCAGAAGTCC-3' | SEQ ID NO:1 | B | 158–175 | i+20: 1–175 |
| ACE/82RB | 5'-CCAGGGAGGTGAAGAAATC-3' | SEQ ID NO:2 | B | 35–53 | e20, J04144 |
| ACE/84FT | 5'-AGCCAGGCAGTAATGACCT-3' | SEQ ID NO:3 | T | 1–19 | i-19: 1–218 |
| ACE/94FB | 5'-GCCCACTGTTCCCTTATG-3' | SEQ ID NO:4 | B | 1–18 | i-21: 1–76 |
| ACE/95RB | 5'-TGCCCTGACTGACAGAGC-3' | SEQ ID NO:5 | B | 105–122 | i+23: 1–122 |
| ACE/96RT | 5'-GCCCTGGTGTGCCTGT-3' | SEQ ID NO:6 | T | 1–16 | i-22: 1–65 |
| ACE/107F | 5'-TGCCTGGATATGTGTTGC-3' | SEQ UD NO:7 | – | 1–18 | i-15: 1–225 |
| ACE/107FB | 5'-TGCCTGGATATGTGTTGC-3' | SEQ ID NO:8 | B | 1–18 | i-15: 1–225 |
| ACE/108RB | 5'-GCCCTCGCCTCTCACT-3' | SEQ ID NO:9 | B | 23–38 | i+16: 1–38 |
| ACE/111RT | 5'-TCCCCTCTCCCTGTACCT-3' | SEQ ID NO:10 | T | 17–34 | i+15: 1–34 |
| ACE/114RB | 5'-GTGCTGGGGTAGGGTAGA-3' | SEQ ID NO:11 | B | 101–118 | i+7: 1–118 |
| ACE/118FT | 5'-TCCCCCTGACCTGGCT-3' | SEQ ID NO:12 | T | 221–236 | i-7: 1–253 |
| ACE/119FB | 5'-GGGGCACCGTGATGTT-3' | SEQ ID NO:13 | B | 1–16 | i-4: 1–120 |
| ACE/119FT | 5'-GGGGCACCGTGATGTT-3' | SEQ ID NO:14 | T | 1–16 | i-4: 1–120 |
| ACE/120RB | 5'-GCCAGAGCCTTTGGTTT-3' | SEQ ID NO:15 | B | 230–246 | i+5: 1–246 |
| ACE/122FB | 5'-TGGAAGAGCCGACTTACA4-3' | SEQ ID NO:16 | B | 1–19 | i-5: 1–78 |
| ACE/123RB | 5'-TCCCAGAGGCAAAGAGG-3' | SEQ ID NO:17 | B | 225–241 | i+4: 1–241 |
| ACE/130F | 5'-GTTTCTACTGCGGCTTCAT-3' | SEQ ID NO:18 | – | 1–19 | i-8: 1–131 |
| ACE/130FB | 5'-GTTTCTACTGCGGCTTCAT-3' | SEQ ID NO:19 | B | 1–19 | i-8: 1–131 |
| ACE/134RB | 5'-TCCTGGAAGAGGGAGTTTC-3' | SEQ ID NO:20 | B | 148–166 | i+9: 1–166 |
| ACE/145F | 5'-GCAGGATGAGAGCAACAAC-3' | SEQ ID NO:21 | – | 1–18 | i-7: 1–253 |
| ACE/146F | 5'-CTGGAGACCACTCCCATCCTTTCT-3' | SEQ ID NO:22 | – | 1–24 | i-17: 1–454 |

TABLE 2-continued

| Name | Sequence | Modification *) | Nucleotides | Numbering according to **) |
|---|---|---|---|---|
| ACE/147R | 5'-GATGTGGCCATCACATTCGTCAGAT-3' SEQ ID NO:23 | — | 1–25 | e17, J04144 |
| ACB/170RT | 5'-CTTCCGTGGGACTCATGT-3' SEQ ID NO:24 | T | 23–40 | i+5: 1–246 |
| ACE/171RT | 5'-TGCACCGTGAGGCTCTA-3' SEQ ID NO:25 | T | 136–152 | i+8: 1–152 |
| ACE/173F | 5'-GCCCAATAGGAGGAAGCA-3' SEQ ID NO:26 | MT | 1–10, 1–9 | i-2: 1–10, e2 |
| ACE/174R | 5'-CCCACCCCATCTCCAAGAA-3' SEQ ID NO:27 | — | 166–184 | i-2: 1–184 |
| ACE/175FB | 5'-GCC-3' | MT, B | 1–3 | i-2: 1–10 |
| ACE/176RT | 5'-TCCCTGATGGGCTGCTCTC-3' SEQ ID NO:28 | T | 65–83 | i-2: 1–184 |
| ACE/177FT | 5'-CAAGGCCCTCAACCAACTC-3' SEQ ID NO:29 | T | 1–19 | i-24: 1–50 |
| ACE/178RB | 5'-TTCCCACAAAAGCTCCAGTG-3' SEQ ID NO:30 | B | 71–90 | i+24: 1–108 |
| ACE/179R | 5'-GGCTCAAAATGGCAAGTGTT-3' SEQ ID NO:31 | — | 89–108 | i+24: 1–108 |
| ACE/180FT | 5'-GGGCCATGTCCTTCTGACTC-3' SEQ ID NO:32 | T | 1–20 | i-25: 1–45 |
| ACE/181RB | 5'-CAGCCTGGAGGGGTTAAGA-3' SEQ ID NO:33 | B | 33–51 | i+25: 1–51 |
| ACE/182R | 5'-CCCTTCTGAGCGAGCTGAGT-3' SEQ ID NO:34 | — | 1–6,1–14 | i-26: 1–6, e26, J04144 |
| ACE/183F | 5'-GGCCATGTTGAGCTACTTCAA-3' SEQ ID NO:35 | — | 83–103 | e25, J04144 |
| ACE/184FB | 5'-CCTCCAGCCTTGGGTCTTAA-3' SEQ ID NO:36 | B | 19–38 | i+25: 1–38 |
| ACE/185RT | 5'-TTCCCATCCCAGTCTCTGGT-3' SEQ ID NO:37 | T | 269–288 | e26, J04144 |
| ACE/188RT | 5'-GGCAGCCTGGTTGATGAGT-3' SEQ ID NO:38 | T | 116–134 | e17, J04144 |
| ACE/192FB | 5'-ATTCCAGCTCTGAAATTCTGA-3' SEQ ID NO:39 | B | 1–23 | i-17: 1–85 |
| ACP/3FT | 5'-GAGCCCCTCCAGCACCTC-3' SEQ ID NO:40 | T | 499–5017 | X94359 |
| ACP/4RB | 5'-ACCCGAGCCTGCCCACC-3' SEQ ID NO:41 | B | 5302–5318 | X94359 |
| ACP/5FT | 5'-GGTCGGGCTGGGAAGATC-3' SEQ ID NO:42 | T | 5232–5249 | X94359 |
| ACP/6RB | 5'-TCGGCTCTGCCCCTTCTC-3' SEQ ID NO:43 | B | 5576–5593 | X94359 + additional downstream sequence |
| ACP/7FT | 5'-GCCCTTTCTCCAGCTTCCTCT-3' SEQ ID NO:44 | T | 5361–5381 | X94359 |
| ACP/8RB | 5'-CGGCGGCAGCAGCAACA-3' SEQ ID NO:45 | B | 5666–5682 additional downstream sequence | X94359 + additional |
| ACP/11FB | 5'-GAGCCCCTCCAGCACCTC-3' SEQ ID NO:46 | B | 499–5017 | X94359 |
| ACP/12RT | 5'-ACCCGAGCCTGCCCACC-3' SEQ ID NO:47 | T | 5302–5318 | X94359 |
| ACP/13FB | 5'-GGTCGGGCTGGGAAGATC-3' SEQ ID NO:48 | B | 5232–5249 | X94359 |
| ACP/14RT | 5'-TCGGCTCTGCCCCTTCTC-3' SEQ ID NO:49 | T | 5576–5593 | X94359 + additional downstream sequence |
| ACP/15FB | 5'-GCCCTTTCTCCAGCTTCCTCT-3' SEQ ID NO:50 | B | 5361–5381 | X94359 |
| ACP/16RT | 5'-CGGCGGCAGCAGCAACA-3' SEQ ID NO:51 | T | 5666–5682 | X94359 + additional downstream sequence |

TABLE 2-continued

| Name | Sequence | Modification *) | | Nucleotides **) | Numbering according to |
|---|---|---|---|---|---|
| ANG/1FT | 5'-ATGGCACTTAAAGGTCAGTTAAT-3' | SEQ ID NO:52 | T | 336–358 | M24686 |
| ANG/2RB | 5'-TACGGAAGCCCAAGAAGTT-3' | SEQ ID NO:53 | B | 726–745 | M24686 |
| ANG/5FT | 5'-CTCCCCAACGGCTGTCTT-3' | SEQ ID NO:54 | T | 797–814 | M24686 |
| ANG/6RB | 5'-AGCAGCAACATCCAGTTCTGT-3' | SEQ ID NO:55 | B | 1119–1139 | M24686 |
| ANG/7FT | 5'-TCCCACGCTCTCTGGACTT-3' | SEQ ID NO:56 | T | 1099–1117 | M24686 |
| ANG/8RB | 5'-CTGATCTCAGCTACACATGGATACTA-3' | SEQ ID NO:57 | B | 1290–1315 | M24686 |
| ANG/15FT | 5'-CCTGTCTTGGGTGACTCTTC-3' | SEQ ID NO:58 | T | 7–26 | M24687 |
| ANG/17FB | 5'-TTCTGGGCTAAATGGTGACA-3' | SEQ ID NO:59 | B | 285–304 | M24686 |
| ANG/18RT | 5'-CTTGTCTTCGGTGTCAAGTTT-3' | SEQ ID NO:60 | T | 675–695 | M24686 |
| ANG/19FB | 5'-GGGAGCCTTGGACCACAC-3' | SEQ ID NO:61 | B | 839–856 | M24686 |
| ANG/20RT | 5'-AGCCTGCATGAACCTGTCAA-3' | SEQ ID NO:62 | T | 1147–1167 | M24686 |
| ANG/21FB | 5'-TGGTGGGCGTGTTCACA-3' | SEQ ID NO:63 | B | 1018–1034 | M24686 |
| ANG/22RT | 5'-GCCAGAGCCAGCAGAGA-3' | SEQ ID NO:64 | T | 1264–1280 | M24686 |
| ANG/29RB | 5'-CCACATTCCAGGGGAGAC-3' | SEQ ID NO:65 | B | 335–352 | M24687 |
| ANG/30FB | 5'-CCTGTCTTGGGTGACTCTTC-3'SEQ ID NO:66 | | B | 7–26 | M24687 |
| ANG/32RT | 5'-CCACATTCCAGGGGAGAC-3' | SEQ ID NO:67 | T | 334–352 | M24687 |
| ANP/1FT | 5'-GTCCCTTCAGTGCCCTAATA-3' | SEQ ID NO:68 | T | 314–334 | X15232 |
| ANP/2RB | 5'-ACAGCCAGATTGAAAGACACA-3' | SEQ ID NO:69 | B | 593–613 | X15232 |
| ANP/3FT | 5'-AACCCTTTTACTGGTCATGTGA-3' | SEQ ID NO:70 | B | 492–513 | X15232 |
| ANP/4RB | 5'-CGCTCATGGGATGTGTGAC-3' | SEQ ID NO:71 | B | 747–765 | X15232 |
| ANP/5FT | 5'-TGTTTTCCCCAGTGTCTATTAGA-3' | SEQ ID NO:72 | T | 686–708 | X15232 |
| ANP/6RB | 5'-GCAGGGTCGAGTTACACATTT-3' | SEQ ID NO:73 | B | 982–1003 | X15232 |
| ANP/7FT | 5'-CCTCAGGCTGTCACACACCTA-3' | SEQ ID NO:74 | T | 909–929 | X15232 |
| ANP/8RB | 5'-CGGCTTACCTTCTGCTGTAGT-3' | SEQ ID NO:75 | B | 1246–1266 | X15232 |
| ANP/9FB | 5'-CTCCTTGAACCTGCTTGTGTT-3' | SEQ ID NO:76 | B | 273–293 | X15232 |
| ANP/10RT | 5'-GCATTGAAAGATGTGCTGTTCT-3' | SEQ ID NO:77 | T | 548–569 | X15232 |
| ANP/11FB | 5'-TAACGACTACAAAAGCAAGTCTTAC-3' | SEQ ID NO:78 | B | 446–469 | X15232 |
| ANP/12RT | 5'-AGAGGGCAGGGGAGAGTCT-3' | SEQ ID NO:79 | T | 805–823 | X15232 |
| ANP/13FB | 5'-GGCAGCAGGGTCAGAAGT-3' | SEQ ID NO:80 | B | 766–783 | X15232 |
| ANP/14RT | 5'-GCTGGAGAGGAGGGTTACAT-3' | SEQ ID NO:81 | T | 1127–1146 | X15232 |
| ANP/15FB | 5'-TGCAAACTTCGGTAAATGTGT-3' | SEQ ID NO:82 | B | 970–990 | X15232 |
| ANP/16RT | 5'-CAGAACAACGGCAGCTTCT-3' | SEQ ID NO:83 | T | 1224–1242 | X15232 |
| AT1/5FT | 5'-ACTGGCTGACTTATGCTTTTTACT-3' | SEQ ID NO:84 | T | 547–570 | S77410 |
| AT1/6RB | 5'-GGGTTGAATTTTGGGACTCATA-3' | SEQ ID NO:85 | B | 884–905 | S77410 |
| AT1/7FT | 5'-GCCAGTTTGCCAGCTATAAT-3' | SEQ ID NO:86 | T | 809–828 | S77410 |
| AT1/8RB | 5'-TGATGCCTAGTTGAATCAATACA-3' | SEQ ID NO:87 | B | 1123–1145 | S77410 |

TABLE 2-continued

| Name | Sequence | | Modification *) | Nucleotides | Numbering according to **) |
|---|---|---|---|---|---|
| AT1/9FT | 5'-GAAGGCTTATGAAATTCAGAAGA-3' | SEQ ID NO:88 | T | 1003–1025 | S77410 |
| AT1/10RB | 5'-AAAGTCGGTTCAGTCCACATAA-3' | SEQ ID NO:89 | B | 1535–1556 | S77410 |
| AT1/16FB | 5'-AAACAGCTTGGTGGTGATAGTC-3' | SEQ ID NO:90 | B | 469–490 | S77410 |
| AT1/17RT | 5'-GCAGGTGACTTTGGCTACAA-3' | SEQ ID NO:91 | T | 762–781 | S77410 |
| AT1/18FB | 5'-CCTGTACGCTAGTGTGTTTCTACT-3' | SEQ ID NO:92 | B | 667–690 | S77410 |
| AT1/19RT | 5'-AGGAAACAGGAAACCCAGTATAT-3' | SEQ ID NO:93 | T | 932–955 | S77410 |
| AT1/22FB | 5'-CTGGATTCCCCACCAAATAT-3' | SEQ ID NO:94 | B | 1090–1109 | S77410 |
| AT1/23RT | 5'-TGCTCCTTCTTTCACAAAATTAC-3' | SEQ ID NO:95 | T | 1438–1460 | S77410 |
| ATP/1FT | 5'-CTTCCGTTATTATGTGTGATATTAGT-3' | SEQ ID NO:96 | T | 1244–1269 | U07144 |
| ATP/2RB | 5'-GCATGTACCTAAAAAGTCCTGTC-3' | SEQ ID NO:97 | B | 1566–1588 | U07144 |
| ATP/5FT | 5'-ATTGGCATATCCATCACCTTAA-3' | SEQ ID NO:98 | T | 1628–1649 | U07144 |
| ATP/6RB | 5'-GATCTCCCAACTCATGCTATGA-3' | SEQ ID NO:99 | B | 1961–1982 | U07144 |
| ATP/7FT | 5'-ATTGGATTCAATTTGCCTACAT-3' | SEQ ID NO:100 | T | 1846–1867 | U07144 |
| ATP/8RB | 5'-TTTGGTAATACAGTTGTGGATCATA-3' | SEQ ID NO:101 | B | 2159–2184 | U07144 |
| ATP/9FT | 5'-TGCAACTTGGGTAGCATGTC-3' | SEQ ID NO:102 | T | 2077–2096 | U07144 |
| ATP/10RB | 5'-AGTCGTCCCGTGTCAACTATC-3' | SEQ ID NO:103 | B | 2370–2390 | U07144 |
| ATP/11FB | 5'-CGTTGTCTTCCGTTATTATGTGT-3' | SEQ ID NO:104 | B | 1238–1260 | U07144 |
| ATP/12RT | 5'-TTATTGCATGTACCTAAAAAGTGTA-3' | SEQ ID NO:105 | T | 1455–1479 | U07144 |
| ATP/15FB | 5'-GCATTCATATAAAGATCAAATCAGT-3' | SEQ ID NO:106 | B | 1600–1624 | U07144 |
| ATP/16RT | 5'-CACCCTGATAACAAAACCAGATA3' | SEQ ID NO:107 | T | 1929–1951 | U07144 |
| ATP/17FB | 5'-CTTTCTGGCATCAACCTCACT-3' | SEQ ID NO:108 | B | 1794–1814 | U07144 |
| ATP/18RT | 5'-ACTTTTAAGGACGAATTAGAGAACT-3' | SEQ ID NO:109 | T | 2214–2238 | U07144 |
| ATP/19FB | 5'-GTCCACCCTTGAATTTCATAAC-3' | SEQ ID NO:110 | B | 2115–2136 | U07144 |
| ATP/20RT | 5'-CCCAACCTCCTCCCTCTC-3' | SEQ ID NO:111 | T | 2396–2413 | U07144 |
| ATP/21FT | 5'-GCTCGCTCTCCCTCACGAC-3' | SEQ ID NO:112 | T | 2310–2328 | U07144 |
| ATP/22RB | 5'-TCCAGCCGCTCCCCATC-3' | SEQ ID NO:113 | B | 2657–2673 | U07144 |
| ATP/23FB | 5'-GCTCGCTCTCCCTCACGAC-3' | SEQ ID NO:114 | B | 2310–2328 | U07144 |
| ATP/24RT | 5'-TCCAGCCGCTCCCCATC-3' | SEQ ID NO:115 | T | 2657–2673 | U07144 |
| ATR/1F | 5'-GCCCCTCAGATAATGTAAGCTC-3' | SEQ ID NO:116 | — | 1353–1374 | S77410 |
| ATR/2R | 5'-AACCGGCACGAAAACTTTACT-3' | SEQ ID NO:117 | — | 1834–1854 | S77410 |
| ATR/3aF | 5'-GCACTTCACTACCAAATGAGCA-3' | SEQ ID NO:118 | — | 1476–1500 | S77410 |
| ATR/4cF | 5'-GCACTTCACTACCAAATGAGCC-3' | SEQ ID NO:119 | — | 1476–1500 | S77410 |

Where indicated, the primers were modified in one of the following ways: (i) a biotin molecule was conjugated to the 5' terminus of the indicated sequence (B); (ii) a sequence of nucleotides derived from M13, 5'-CAGGAAACAGCTATGACT-3' (SEQ ID NO: 120), was added at the 5' terminus of the indicated sequence (MT); or (iii) the sequence 5'-AGTCACGACGTTGTAAAACGACGGCCAGT-3' (SEQ ID NO: 121). was added at the 5' terminus of the indicated sequence (T=Tail). Nucleotides were numbered according to the Genbank sequences listed in Table 1 where indicated. When the sequences involved were not publicly available, the numbering was as in the following examples: The designation "i-4: 1–200" indicates that the primer sequence is located within the sequence extending 200 bp upstream of, and including, the nucleotide immediately upstream of the first coding nucleotide of exon 4. Similarly, the designation "i+4: 1–200" indicates that the primer sequence is located within the sequence extending from the nucleotide that is located immediately downstream of the last coding nucleotide of exon 4 downstream for 200 bp. In each case, the specific location of the primer sequence is indicated in Table 2 in the column marked "Nucleotides".

The reaction components used for PCR are described in Table 3 below.

TABLE 3

| Condition | Components | Volume |
|---|---|---|
| A | Ultrapure dNTP Set 2.5 mM (dATP:dCTP:dGTP:dTTP = 1:1:1:1), (Pharmacia Biotech) | 4 μl |
|  | 10xPCR buffer II, (Perkin Elmer) | 5 μl |
|  | MgCl$_2$ solution 2.5 mM, | 3 μl |
|  | AmpliTaq ® DNApolymerase (Perkin Elmer) (5U/ml) | 0.15 μl |
|  | Primer 1 | 1 μl |
|  | Primer 2 | 1 μl |
|  | DNA solution | 1 μl |
|  | R/O-purified water q.s. | Tot. 50 μl |
| B | Ultrapure dNTP Set 2.5 mM (dATP:dCTP:dGTP:dITP:dTTP = 2:2:1:1:2), (Pharmacia Biotech) | 4 μl |
|  | 10xPCR buffer II, (Perkin Elmer) | 5 μl |
|  | MgCl$_2$ solution 2.5 mM, (Perkin Elmer) | 3 μl |
|  | AmpliTaq ® DNApolymerase (5U/ml) | 0.15 μl |
|  | Primer 1 | 1 μl |
|  | Primer 2 | 1 μl |
|  | DNA solution | 1 μl |
|  | R/O-purified water q.s. | Tot. 50 μl |
| C | Ultrapure dNTP Set 2.5 mM (dATP:dCTP:dGTP:dITP:dTTP = 4:4:1:3:4), (Pharmacia Biotech) | 4 μl |
|  | 10xPCR buffer II, (Perkin Elmer) | 5 μl |
|  | MgCl$_2$ solution 2.5 mM, (Perkin Elmer) | 3 μl |
|  | AmpliTaq ® DNApolymerase (5U/ml) | 0.15 μl |
|  | Primer 1 | 1 μl |
|  | Primer 2 | 1 μl |
|  | DNA solution | 1 μl |
|  | R/O-purified water q.s. | Tot. 50 μl |
| D | Ultrapure dNTP Set 2.5 mM (dATP:dCTP:dGTP:dITP:dTTP = 6:6:1:5:6), (Pharmacia Biotech) | 4 μl |
|  | 10xPCR buffer II, (Perkin Elmer) | 5 μl |
|  | MgCl$_2$ solution 2.5 mM, (Perkin Elmer) | 3 μl |
|  | AmpliTaq ® DNApolymerase (5U/ml) | 0.15 μl |
|  | Primer 1 | 1 μl |
|  | Primer 2 | 1 μl |
|  | DNA solution | 1 μl |
|  | R/O-purified water q. s. | Tot. 50 μl |
| E | Ultrapure dNTP Set 2.5 mM | 4 μl |

TABLE 3-continued

| Condition | Components | Volume |
|---|---|---|
|  | (dATP:dCTP:dGTP:dITP:dTTP = 4:4:1:3:4), (Pharmacia Biotech) |  |
|  | 10xPCR buffer II, (Perkin Elmer) | 5 μl |
|  | MgCl$_2$ solution 2.5 mM, (Perkin Elmer) | 2.5 μl |
|  | DMSO | 2.5 μl |
|  | AmpliTaqGold ® DNApolymerase (5U/ml) | 0.5 μm |
|  | Primer 1 | 1 μl |
|  | Primer 2 | 1 μl |
|  | DNA solution | 1 μl |
|  | R/O-purified water q.s. | Tot. 50 μl |
| F | Ultrapure dNTP Set 2.5 mM (dATP:dCTP:dGTP:dTTP = 1:1:1:1) (Pharmacia Biotech) | 4 μl |
|  | 10xPCR buffer II, (Perkin Elmer) | 5 μl |
|  | MgCl$_2$ solution 2.5 mM, (Perkin Elmer) | 2 μl |
|  | AmpliTaq ® DNApolymerase (5U/ml) | 0.5 μl |
|  | Primer 1 | 1 μl |
|  | Primer 2 | 1 μl |
|  | DNA solution | 1 μl |
|  | R/O-purified water q.s. | Tot. 50 μl |
| G | Ultrapure dNTP Set 2.5 mM (dATP:dCTP:dGTP:dTTP = 1:1:1:1) (Pharmacia Biotech) | 4 μl |
|  | 10xPCR buffer II, (Perkin Elmer) | 5 μl |
|  | MgCl$_2$ solution 2.5 mM, (Perkin Elmer) | 2 μl |
|  | AmpliTaq ® DNApolymerase (5U/ml) | 0.5 μl |
|  | Primer 1 | 1 μl |
|  | Primer 2 | 1 μl |
|  | DNA solution | 1 μl |
|  | R/O-purified water q.s. | Tot. 50 μl |
| H | Ultrapure dNTP Set 2.5 mM (dATP:dCTP:dGTP:dITP:dTTP = 4:4:1:3:4), (Pharmacia Biotech) | 4 μl |
|  | 10xPCR buffer II, (Perkin Elmer) | 5 μl |
|  | MgCl$_2$ solution 2.5 mM, (Perkin Elmer) | 4 μl |
|  | AmpliTaqGold ® DNApolymerase (5U/ml) | 0.5 μl |
|  | Primer 1 | 1 μl |
|  | Primer 2 | 1 μl |
|  | DNA solution | 1 μl |
|  | R/O-purified water q.s. | Tot. 50 μl |

TABLE 4

| PCR-method | Temperature*) | Time*) | Temperature**) | Time | Temperature | Time | No of cycles***) |
|---|---|---|---|---|---|---|---|
| 25 | 94 | 15 s | 55 | 30 s | 72 | 45 s | 35 |
|  | 72 | 5 min |  |  |  |  | 1 |
|  | 22 | ∞ |  |  |  |  |  |
| 27 | 94 | 15 s | 55 | 30 s | 72 | 45 s | 35 |
|  | 72 | 5 min |  |  |  |  | 1 |
|  | 22 | ∞ |  |  |  |  |  |
| 36 | 94 | 2 min |  |  |  |  | 1 |
|  | 94 | 15 s | 58 | 30 s | 72 | 45 s | 35 |
|  | 72 | 5 min |  |  |  |  | 1 |
|  | 22 | ∞ |  |  |  |  |  |
| 38 | 94 | 2 min |  |  |  |  | 1 |
|  | 94 | 15 s | 60 | 30 s | 72 | 45 s | 15 |
|  | 72 | 5 min |  |  |  |  | 1 |
|  | 22 | ∞ |  |  |  |  |  |
| 40 | 94 | 2 min |  |  |  |  | 1 |

TABLE 4-continued

| PCR-method | Temperature*) | Time*) | Temperature**) | Time | Temperature | Time | No of cycles***) |
|---|---|---|---|---|---|---|---|
|  | 94 | 15 s | 60 | 30 s | 72 | 45 s | 35 |
|  | 72 | 5 min |  |  |  |  | 1 |
|  | 22 | ∞ |  |  |  |  |  |
| 54 | 96 | 5 min |  |  |  | 1 |  |
|  | 96 | 30 s | 61 | 30 s | 72 | 45 s | 15 |
|  | 72 | 5 min |  |  |  |  | 1 |
|  | 22 | ∞ |  |  |  |  |  |
| 56 | 96 | 5 min |  |  |  |  | 1 |
|  | 96 | 30 s | 61 | 30 s | 72 | 45 s | 35 |
|  | 72 | 5 min |  |  |  |  | 1 |
|  | 22 | ∞ |  |  |  |  |  |
| 64 | 95 | 2 min |  |  |  |  |  |
|  | 95 | 15 s | 59 | 30 s | 72 | 45 s | 40 |
|  | 72 | 5 min |  |  |  |  | 1 |
|  | 22 | ∞ |  |  |  |  |  |
| 70 | 95 | 5 min |  |  |  |  |  |
|  | 95 | 15 s | 59 | 30 s | 72 | 45 s | 50 |
|  | 72 | 5 min |  |  |  |  | 1 |
|  | 22 | ∞ |  |  |  |  |  |

All temperatures are given in degrees Celsius.
*)indicates the default initial temperatures (° C.) and times of the program.
**)indicates the default temperature (° C.) of the program.
***)indicates the default number of cycles of the program, referring to the section of the PCR program where three different temperatures are employed.

Any differences are indicated in "Modifications" in Table 5 below.

The amplified fragments are described in Table 5 below with respect to the primers and PCR reaction conditions used for amplification.

TABLE 5

| Fragment | | Primer 1 | Primer 2 | PCR method | Modifications of PCR method | PCR reaction conditions |
|---|---|---|---|---|---|---|
| ANPf1F |  | ANP/1FT | ANP/2RB | 64 |  | A |
| ANPf2F |  | ANP/3FT | ANP/4RB | 64 |  | B |
| ANPf3F |  | ANP/5FT | ANP/6RB | 64 | anneal. temp: 48° C. | A |
| ANPf4F |  | ANP/7FT | ANP/8RB | 64 | anneal. temp: 59° C. | D |
| ANPf5R |  | ANP/9FB | ANP/10RT | 64 |  | A |
| ANPf6R |  | ANP/11FB | ANP/12RT | 64 |  | B |
| ANPf7R |  | ANP/13FB | ANP/14RT | 64 |  | A |
| ANPf8R |  | ANP/15FB | ANP/16RT | 64 |  | C |
| ANGe2f1F |  | ANG/1FT | ANG/2RB | 64 |  | C |
| ANGe2f3F |  | ANG/5FT | ANG/6RB | 64 |  | C |
| ANGe2f4F |  | ANG/7FT | ANG/8RB | 64 |  | A |
| ANGe2f5R |  | ANG/17FB | ANG/18RT | 64 |  | A |
| ANGe2f7R |  | ANG/19FB | ANG/20RT | 64 |  | A |
| ANGe2f8R |  | ANG/21FB | ANG/22RT | 64 |  | A |
| ANGe3F |  | ANG/15FT | ANG/29RB | 64 | anneal. temp: 57° C. | F |
| ANGe3R |  | ANG/30FB | ANG/32RT | 64 | anneal. temp: 57° C., 45 cycles | A |
| ACPf2F |  | ACP/3FT | ACP/4RB | 70 | anneal. temp: 62° C. | E |
| ACPf3F |  | ACP/5FT | ACP/6RB | 70 | anneal. temp: 58° C. | E |
| ACPf4F |  | ACP/7FT | ACP/8RB | 70 |  | E |
| ACPf6R |  | ACP/11FB | ACP/12RT | 70 | anneal. temp: 62° C. | E |
| ACPf7R |  | ACP/13FB | ACP/14RT | 70 | anneal. temp: 58° C. | E |
| ACPf8R |  | ACP/15FB | ACP/16RT | 70 |  | E |
| ACEe2R | PCR1 | ACE/173F | ACE/174R | 38 |  | A |
| ACEe2R | PCR2 | ACE/175FB | ACE/176RT | 40 |  | A |
| ACEe4F | PCR1 | ACE/119FB | ACE/120RB | 27 |  | A |
| ACEe4F | PCR2 | ACE/119FT | ACE/123RB | 25 |  | A |
| ACEe5R | PCR1 | ACE/119FB | ACE/120RB | 27 |  | A |
| ACEe5R | PCR2 | ACE/122FB | ACE/170RT | 25 |  | A |
| ACEe7F | PCR1 | ACE/145F | ACE/114RB | 27 |  | A |
| ACEe7F | PCR2 | ACE/118FT | ACE/114RB | 25 |  | A |
| ACEe8R | PCR1 | ACE/130F | ACE/134RB | 27 |  | A |
| ACEe8R | PCR2 | ACE/130FB | ACE/171RT | 25 |  | A |
| ACEe15R | PCR1 | ACE/107F | ACE/108RB | 27 |  | A |
| ACEe15R | PCR2 | ACE/107FB | ACE/111RT | 25 |  | A |
| ACEe17R |  | ACE/192FB | ACE/188RT | 40 | anneal. temp: 63° C., 40 cycles | A |

TABLE 5-continued

| Fragment | | Primer 1 | Primer 2 | PCR method | Modifications of PCR method | PCR reaction conditions |
|---|---|---|---|---|---|---|
| ACEe19F | PCR1 | ACE/84FT | ACE/79RB | 27 | | A |
| ACEe19F | PCR2 | ACE/84FT | ACE/82RB | 25 | | A |
| ACEe21R | PCR1 | ACE/94FB | ACE/95RB | 27 | | A |
| ACEe21R | PCR2 | ACB/94FB | ACE/96RT | 25 | | A |
| ACEe24F | PCR1 | ACE/177FT | ACE/179R | 38 | | A |
| ACEe24F | PCR2 | ACE/177FT | ACE/178RB | 40 | | A |
| ACEe25F | PCR1 | ACE/180FT | ACE/182R | 38 | | A |
| ACEe25F | PCR2 | ACE/180FT | ACE/181RB | 40 | | A |
| ACEe26R | PCR1 | ACE/183F | ACE/185RT | 54 | | A |
| ACEe26R | PCR2 | ACE/184FB | ACE/185RT | 56 | | A |
| ACEDI | | ACE/146F | ACE/147R | 36 | | A |
| ATPf1F | | ATP/1FT | ATP/2RB | 64 | | A |
| ATPf3F | | ATP/5FT | ATP/6RB | 64 | anneal. temp: 58° C. | A |
| ATPf4F | | ATP/7FT | ATP/8RB | 64 | anneal. temp: 48° C. | A |
| ATPf5F | | ATP/9FT | ATP/10RB | 64 | anneal. temp: 58° C. | A |
| ATPf6R | | ATP/11FB | ATP/12RT | 64 | anneal. temp: 48° C. | A |
| ATPf8R | | ATP/15FB | ATP/16RT | 64 | anneal. temp: 55° C. | G |
| ATPf9R | | ATP/17FB | ATP/18RT | 64 | anneal. temp: 54° C. | A |
| ATPf10R | | ATP/19FB | ATP/20RT | 64 | | A |
| ATPf11F | | ATP/21FT | ATP/22RB | 64 | initial denaturation: 95° C., 12 min. | H |
| ATPf12R | | ATP/23FB | ATP/24RT | 64 | initial denaturation: 95° C., 12 min. | H |
| AT1e5f2F | | AT1/5FT | AT1/6RB | 64 | | A |
| AT1e5f3F | | AT1/7FT | AT1/8RB | 64 | | A |
| AT1e5f4F | | AT1/9FT | AT1/10RB | 64 | | C |
| AT1e5f6R | | AT1/16FB | AT1/17RT | 64 | | A |
| AT1e5f7R | | AT1/18FB | AT1/19RT | 64 | | C |
| AT1e5f9R | | AT1/22FB | AT1/23RT | 64 | | A |
| AT1-spec. 1 | | ATR/1F ATR/3aF | ATR/2R | 40 | anneal. temp: 63° C. | A |
| AT1-spec. 2 | | ATR/1F ATR/2R | ATR/4cF | 40 | anneal. temp: 63° C. | A |

All of the PCR products (except fragments ACEDI, AT1-spec. 1 and AT1-spec. 2) were subjected to solid phase sequencing according to the protocol commercially available from Pharmacia Biotech. The sequencing reactions are performed with a sequencing primer having a complementary sequence to the "Tail" sequence previously described in Table 2. The nucleotide sequence of the sequencing primer was 5'-CGACGTTGTAAAACGACGGCCAGT-3' (SEQ ID NO: 122), and the primer was fluorescently labeled with a Cy-5-molecule on the 5'-nucleotide. The positions carrying a genetic variation were identified by determination of the nucleotide sequence by the use of the ALFexpress™ system commercially available from Pharmacia Biotech.

The detection of the fragment ACEDI was performed by analyzing the sizes of the amplified fragments by gel electrophoresis, where the presence of a shorter PCR product (192 base pairs) indicated the D-allele and a longer PCR product (479 base pairs) indicated the I-allele. The presence of both bands indicated a heterozygote for the two alleles. The detection of the allele-specific reaction of position AT1-1271 was performed by separately running two parallel PCR reactions on the same sample and comparing the sizes of the amplified fragments. A PCR product of 501 base pairs should always be present as a control in both parallel runs, whereas the presence of a PCR product of 378 base pairs in the reaction designated AT1-spec. 1 indicated the presence of an A in this position. The presence of a PCR product of 378 base pairs in the reaction designated AT1-spec. 2 indicated a C in this position. If the shorter PCR product was present in both reactions, the individual is a heterozygote for A and C.

Results:

The analysis described above resulted in the identification of polymorphic positions within the regulatory and coding/intron segments of the human genes encoding ACE, AGT, and AT1. The polymorphic positions, the variant nucleotides found at each of the positions, and the PCR fragment in which the polymorphism was identified are shown in Table 6 below. Also shown are the frequencies of each genotype in a population of 90 individuals, expressed as the percent of the study population having that genotype. Polymoiphisms that resulted in alternate amino acids in ACE, AGT, or AT1 are also indicated. As used herein below, the designations "AGR", "ACR", and "ATR" refer to the regulatory regions of the human AGT, ACE, and AT1 genes, respectively; and the designations "AGT", "ACE", and "AT1", refer to the coding regions of the AGT, ACE, and AT1 genes.

TABLE 6

| Gene | Position | Reported genotype | Genetic variation | Frequency (percent) | Amino acid change | Fragment | Reference (if any) |
|---|---|---|---|---|---|---|---|
| AGR | 395 | T | TT-TA-AA | 88-11-1 | None | ANPf1F ANPf5R | — |
| AGR | 412 | C | CC-CT | 99-1 | None | ANPf1F ANPf5R | — |
| AGR | 432 | G | GG-GA | 81-19 | None | ANPf1F | — |

TABLE 6-continued

| Gene | Position | Reported genotype | Genetic variation | Frequency (percent) | Amino acid change | Fragment | Reference (if any) |
|---|---|---|---|---|---|---|---|
| AGR | 449 | C | TT-TC | 92-8 | None | ANPf5R ANPf1F | — |
| AGR | 692 | C | CC-CT | 81-19 | None | ANPf5R ANPf2F | — |
| AGR | 839 | G | GG-GA | 93-7 | None | ANPf6R ANPf3F | — |
| AGR | 1007 | G | GG-GA | 81-19 | None | ANPf7R ANPf4F | — |
| AGR | 1072 | G | GG-GA | 89-11 | None | ANPf7R ANPf4F | — |
| AGR | 1204 | C | CC-CA-AA | 67-33 | None | ANPf7R ANPf4F | — |
| AGR | 1218 | A | AA-AG-GG | 14-55-31 | None | ANPf8R ANPf4F ANPf8R | Inuoe, I et. al. J. C. I. (1997) 99:1786–1789. |
| AGT | 273 | C | CC-CT | 99-1 | None | ANGe2f1F ANGe2f5R | — |
| AGT | 620 | C | CC-CT | 80-20 | Thr-Met | ANGe2f3F ANGe2f7R | JeunmaîtreX, et al. Cell (1992) 71:169–180. |
| AGT | 803 | T | TT-TC-CC | 35-52-13 | Met-Thr | ANGe2f4F ANGe2f8R | JeunmaîtreX, et al. Cell (1992) 71:169–180. |
| AGT | 912 | C | CC-CT | 99-1 | None | ANGe3F ANGe3R | — |
| AGT | 997 | G | CC | 100 | Glu-Gln | ANGe3F ANGe3R | — |
| AGT | 1116 | G | GG-GA-AA | 87-12-1 | None | ANGe3F ANGe3R | — |
| AGT i3 | 49 Numbering according to GenBank entry M24688 | A | AA-AG | 80-20 | None | ANGe3F ANGe3R | — |
| AGT | 1174 | C | CC-CA | 99-1 | Leu-Met | ANGe4F ANGe4R | — |
| ACR | 5106 | C | CC-CT | 98-2 | None | ACPf2F ACPf6R | — |
| ACR | 5349 | A | AA-AT-TT | 35-46-19 | None | ACPf3F ACPf7R | Villard, E. et al. Am. J. Hum. Genet. (1996) 58: 1268–1278 |
| ACR | 5496 | T | TT-TC-CC | 35-46-19 | None | ACPf4F ACPf8R | Villard, E. et al. Am. J. Hum. Genet. (1996) 58: 1268–1278 |
| ACE | 375 | A | CC | 100 | None | ACEe2R | — |
| ACE | 582 | C | CC-CT | 94-6 | None | ACEe4F | — |
| ACE | 731 | A | AA-AG | 96-4 | Tyr-Cys | ACEe5R | — |
| ACE | 1060 | G | GG-GA | 97-3 | Gly-Arg | ACEe7F | — |
| ACE | 1215 | C | CC-CT-TT | 35-42-23 | None | ACEe8R | Villard, E. et al. Am. J. Hum. Genet. (1996) 58: 1268–1278 |
| ACE | 2193 | G | GG-GA-AA | 20-57-23 | None | ACEe15R | Villard, E. et al. Am. J. Hum. Genet. (1996) 58: 1268–1278 |
| ACE | 1451 | | DD-DI-II | 29-54-20 | None | ACEDI | Villard, E. et al. Am. J. Hum. Genet. (1996) 58: 1268–1278 |
| ACE | 2328 | A | AA-AG-GG | 20-57-23 | None | ACEe17R | Villard, E. et al. Am. J. Hum. Genet. (1996) 58: 1268–1278 |
| ACE | 2741 | G | TT | 100 | Gly-Val | ACEe19F | — |
| ACE | 3132 | C | CC-CT | 99-1 | None | ACEe21R | — |
| ACE | 3387 | T | TT-TC-CC | 20-57-23 | None | ACEe24F | — |
| ACE | 3503 | C | GG | 100 | Ala-Gly | ACEe25F | — |
| ACE | 3906 | G | GG-GA | 91-9 | None | ACEe26R | — |
| ATR | 1427 | A | AA-AT-TT | 77-22-1 | None | ANPf1F ANPf6R | — |
| ATR | 1756 | T | TT-TA-AA | 75-24-1 | None | ANPf3F ANPf8R | — |
| ATR | 1853 | T | TT-TG-GG | 82-11-1 | None | ANPf3F ANPf8R | — |
| ATR | 2046 | T | CC-CT-TT | 46-46-8 | None | ANPf4F ANPf9R | — |
| ATR | 2354 | A | AA-AC-CC | 73-26-1 | None | ANPf5F ANPf10R | — |
| ATR | 2355 | G | GG-GC-CC | 73-26-1 | None | ANPf5F ANPf10R | — |

TABLE 6-continued

| Gene | Position | Reported genotype | Genetic variation | Frequency (percent) | Amino acid change | Fragment | Reference (if any) |
|---|---|---|---|---|---|---|---|
| ATR | 2415 | A | AA-AG | 75-24-1 | None | ANPf11F ANPf12R | — |
| AT1 | 449 | G | GG-GC | 99-1 | Ser-Thr | AT1e5f2F AT1e5f6R | — |
| AT1 | 678 | T | CC-CT-TT | 31-48-21 | None | AT1e5f3F AT1e5f7R | Rolfs A, et. al. Eur. Heart. J. (1994) 15: Suppl. D, 108–112. |
| AT1 | 1167 | A | AA-AG | 92-8 | None | AT1e5f4F AT1e5f9R | Rolfs A, et. al. Eur. Heart. J. (1994) 15: Suppl. D, 108–112. |
| AT1 | 1271 | A | AA-AC-CC | 50-40-10 | None | AT1-spec | Bonnardeaux, A. et al. Hypertension (1994) 24:63–69. |

A subset of these polymorphic positions were further analyzed in an additional 187 individuals. Table 7 shows the polymorphic positions, the sequence at these positions, and the genotype frequencies for each position in a population of 277 as described in Example 1 above.

TABLE 7

| Gene | Position | Genetic variation | Frequency (per cent) |
|---|---|---|---|
| AGR | 395 | TT-TA-AA | 87-12-7 |
| AGR | 432 | GG-GA-AA | 78-21-1 |
| AGR | 449 | TT-TC-CC | 94-5-1 |
| AGR | 692 | CC-CT-TT | 78-21-1 |
| AGR | 839 | GG-GA | 96-4 |
| AGR | 1007 | GG-GA-AA | 78-21-1 |
| AGR | 1072 | GG-GA | 76-24 |
| AGR | 1204 | CC-CA-AA | 3-27-70 |
| AGR | 1218 | AA-AG-GG | 16-5O-34 |
| AGT | 620 | CC-CT-TT | 75-23-2 |
| AGT | 803 | TT-TC-CC | 34-5O-16 |
| AGT | 1116 | GG-GA-AA | 83-15-2 |
| ACR | 5349 | AA-AT-TT | 37-44-19 |
| ACR | 5496 | TT-TC-CC | 38-43-19 |
| ACE | 1060 | GG-GA | 96-4 |
| ACE | 1215 | CC-CT-TT | 34-46-20 |
| ACE | 2193 | GG-GA-AA | 22-53-25 |
| ACE | 2328 | AA-AG-GG | 23-52-25 |
| ACE | 3387 | TT-TC-CC | 24-53-23 |
| ACE | 3906 | GG-GA-AA | 86-13-1 |
| ATR | 1427 | AA-AT-TT | 72-26-2 |
| ATR | 1756 | TT-TA-AA | 72-25-3 |
| ATR | 1853 | TT-TG-GG | 73-25-2 |
| ATR | 2046 | CC-CT-TT | 47-41-12 |
| ATR | 2354 | AA-AC-CC | 72-26-2 |
| ATR | 2355 | GG-GC-CC | 71-27-2 |
| ATR | 2415 | AA-AG-GG | 73-25-2 |
| AT1 | 678 | CC-CT-TT | 26-51-23 |
| AT1 | 1167 | AA-AG | 88-12 |
| AT1 | 1271 | AA-AC-CC | 55-36-9 |

EXAMPLE 2

Correlation of Polymorphic Patterns with Cardiovascular Disease

The polymorphic positions identified as in Example 1 were correlated with the following markers of cardiovascular status present in the study population: myocardial infarction (MI); stroke; and high blood pressure. Polymorphic patterns, i.e., combinations of sequences at particular polymorphic positions, that show a statistically significant correlation with one or more of these markers are shown below.

|  | Healthy (100) | MI (120) | Stroke (37) | High BP (39) | Total (n) |
|---|---|---|---|---|---|
| ACR 5349 A/T, AGR 1218 A | | | | | |
| # of events | 3 | 7 | 3 | 5 | 17 |
| % within group | 3 | 5.8 | 8.1 | 12.8 | |
| ACR 5496 C, AGR 1204 A/C | | | | | |
| # of events | 2 | 7 | 3 | 2 | 13 |
| % within group | 2 | 5.8 | 8.1 | 5.1 | |
| ACR 5496 C/T, AGR 1218 A, AGT 620 C/T | | | | | |
| # of events | 4 | 13 | 1 | 3 | 21 |
| % within group | 4 | 10.8 | 2.7 | 7.7 | |
| ACE 2193 A, AGR 1204 C, ACE 2328 G | | | | | |
| # of events | 0 | 11 | 3 | 3 | 16 |
| % within group | 0 | 9.2 | 8.1 | 7.7 | |
| ACE 2193 A, AGR 1204 A/C | | | | | |
| # of events | 1 | 1 | 0 | 1 | 3 |
| % within group | 1 | 0.8 | 0 | 2.6 | |
| ACE 3387 T, AGR 1218 A | | | | | |
| # of events | 2 | 4 | 1 | 3 | 10 |
| % within group | 2 | 3.3 | 2.7 | 7.7 | |
| ACE 3387 T, AGT 620 C/T | | | | | |
| # of events | 1 | 10 | 3 | 2 | 15 |
| % within group | 1 | 8.3 | 8.1 | 5.1 | |
| AGR 1204 A/C, AT1 678 C/T | | | | | |
| # of events | 5 | 23 | 5 | 6 | 37 |
| % within group | 5 | 19.2 | 13.5 | 15.4 | |
| AGR 1204 A/C, AT1 1271 A/C | | | | | |
| # of events | 3 | 17 | 3 | 4 | 26 |
| % within group | 3 | 14.2 | 8.1 | 10.3 | |
| ACE 1215 C, AGR 1204 A/C | | | | | |
| # of events | 3 | 13 | 5 | 6 | 25 |
| % within group | 3 | 10.8 | 13.5 | 15.4 | |
| AGR 1204 A/C, AT1 1167 A, ACE 3906 A/G | | | | | |
| # of events | 0 | 5 | 1 | 0 | 6 |
| % within group | 0 | 4.2 | 2.7 | 0 | |
| AGR 1204 A, AGT 620 C, AT1 1271 A, AT1 1167 A, AGR 395 A/T | | | | | |
| # of events | 1 | 4 | 5 | 3 | 11 |
| % within group | 1 | 3.3 | 13.5 | 7.7 | |
| AGR 1204 A/C, AGT 620 C/T, AT1 1271 A/C, AT1 1167 A, AGR 395 T | | | | | |
| # of events | 3 | 13 | 3 | 2 | 20 |
| % within group | 3 | 10.8 | 8.1 | 5.1 | |

| | Healthy (100) | MI (120) | Stroke (37) | High BP (39) | Total (n) |
|---|---|---|---|---|---|
| AGR 1204 A/C, AGT 620 C/T, AT1 1271 A/C, AT1 1167 A/G, AGR 395 T | | | | | |
| # of events | 0 | 2 | 0 | 1 | 3 |
| % within group | 0 | 1.7 | 0 | 2.6 | |
| Summary of the three previous polymorphic patterns (which involve the same polymorphic positions): | | | | | |
| # of events | 4 | 19 | 8 | 6 | 34 |
| % within group | 4 | 15.8 | 21.6 | 15.4 | |
| AGR 1204 A, AT1 678 C, AT1 1167 A, AGR 395 A/T | | | | | |
| # of events | 1 | 2 | 2 | 1 | 5 |
| % within group | 1 | 1.7 | 5.4 | 2.6 | |
| AGR 1204 A/C, AT1 678 C/T, AT1 1167 A, AGR 395 T | | | | | |
| # of events | 3 | 18 | 5 | 4 | 28 |
| % within group | 3 | 15.0 | 13.5 | 10.3 | |
| Summary of the two previous polymorphic patterns: | | | | | |
| # of events | 4 | 20 | 7 | 5 | 33 |
| % within group | 4 | 16.7 | 18.9 | 12.8 | |
| AGT 620 C/T, AT1 1271 A/C, AT1 1167 A, AGR 395 T | | | | | |
| # of events | 2 | 8 | 1 | 2 | 13 |
| % within group | 2 | 6.7 | 2.7 | 5.1 | |
| AGT 620 C/T, AT1 1271 A/C, AT1 1167 A/G, AGR 395 T | | | | | |
| # of events | 0 | 2 | 0 | 1 | 3 |
| % within group | 0 | 1.7 | 0 | 2.6 | |
| AGT 620 C, AT1 1271 A, AT1 1167 A, AGR 395 A/T | | | | | |
| # of events | 1 | 4 | 5 | 3 | 11 |
| % within group | 1 | 3.3 | 13.5 | 7.7 | |
| Summary of the three previous polymorphic patterns: | | | | | |
| # of events | 3 | 14 | 6 | 6 | 27 |
| % within group | 3 | 11.7 | 16.2 | 15.4 | |
| AGT 620 C, AT1 678 A, AT1 1167 A, AGR 395 A/T | | | | | |
| # of events | 1 | 2 | 2 | 1 | 5 |
| % within group | 1 | 1.7 | 5.4 | 2.6 | |
| AGT 620 C/T, AT1 678 C/T, AT1 1167 A, AGR 395 T | | | | | |
| # of events | 3 | 15 | 4 | 4 | 24 |
| % within group | 3 | 12.5 | 10.8 | 10.3 | |
| Summary of the two previous polymorphic patterns: | | | | | |
| # of events | 4 | 17 | 6 | 5 | 29 |
| % within group | 4 | 14.2 | 16.2 | 12.9 | |
| ACE 2193 A, AGR 1218 A, AGT 803 A | | | | | |
| # of events | 2 | 5 | 1 | 3 | 11 |
| % within group | 2 | 4.2 | 2.7 | 7.7 | |
| ACE 2193 A, AGT 620 C/T | | | | | |
| # of events | 1 | 11 | 3 | 2 | 16 |
| % within group | 1 | 9.2 | 8.1 | 5.1 | |
| ACE 2328 G, AGT 620 C/T | | | | | |
| # of events | 1 | 11 | 3 | 2 | 16 |
| % within group | 1 | 9.2 | 8.1 | 5.1 | |
| ACE 3387 T, AGR 1204 A/C | | | | | |
| # of events | 0 | 10 | 3 | 3 | 15 |
| % within group | 0 | 8.3 | 8.1 | 7.7 | |

EXAMPLE 3

Correlation Between a Specific Polymorphic Pattern and Treatment Response

The following study was undertaken to define polymorphic patterns in the human ACE, AGT, and/or AT1 genes that predict the efficacy of treatments for cardiovascular disease. Two groups of hypertensive patients were studied, 41 in the first group and in the second group. The groups were analyzed independently and in combination.

The patients in this population were each treated with one of the following five ACE inhibitors: Captopril, Trandolapril, Lisinopril, Fosinopril, or Enalapril. The effect of the drugs on mean arterial blood pressure was quantified. Mean arterial blood pressure was defined as $\frac{2}{3}$ of the diastolic blood pressure+$\frac{1}{3}$ of systolic blood pressure. The individuals were also categorized as "high responders," i.e., those exhibiting a decrease of more than 16 mm Hg during treatment with an ACE inhibitor drug, and "low responders," i.e., those not exhibiting a decrease of more than 16 mm Hg.

One particular polymorphic pattern, ACE 2193 A/G, AGR 1072 G/A, AT1 1167 A/G, which was present in 51% of the first study population, discriminated between high responders and low responders. In the second group of 20 patients, the pattern was less prevalent (25%), but the correlation with lowered blood pressure was evident. Individuals having this polymorphic pattern (designated "1" below) experienced a larger decrease in blood pressure than those lacking this polymorphic pattern (designated "0" below).

| Polymorphic Pattern | Observations | Mean (mm Hg) Change in B.P. | S.D. |
|---|---|---|---|
| 0 | 36 | −11.4 | 8.6 |
| 1 | 25 | −18.1 | 9.7 |

Furthermore, the distribution of high responders and low responders (as defined above) was as follows:

| Polymorphic Pattern | Low responder % | High responder % |
|---|---|---|
| 0 | 80.1 | 19.4 |
| 1 | 24.0 | 76.0 |

Taken together, the results from the two groups indicate that the presence of this polymorphic pattern correlates with an incremental decrease of 6.4–7.3 mm Hg relative to individuals not having this polymorphic pattern.

The prevalence of this polymorphic pattern was 41% in this hypertensive population. This suggests that testing for this polymorphic pattern in hypertensive patients, followed by prescribing ACE inhibitors only to those patients having this polymorphic pattern, could increase the response rate from 43% (in a hypertensive population in general) to 76% in hypertensive population selected according to the methods of the invention.

What is claimed is:

1. An isolated nucleic acid derived from the human gene encoding angiotensin coverting enzyme (ACE), wherein said nucleic acid comprises a polymorphic position selected from the group consisting of a position in the regulatory region (SEQ ID NO: 129) numbered 5106; positions in the coding region (SEQ ID NO: 130) numbered 375, 582, 731, 1060, 2741, 3132, 3387, 3503, and 3906; and combinations of any of the foregoing.

2. A nucleic acid as defined in claim 1 wherein the sequence at said polymorphic position in the regulatory region is selected from the group consisting of 5106C and 5106T; and the sequence at said polymorphic position in the coding region is selected from the group consisting of 375A, 375C, 582C, 582T, 731A, 731G, 1060G, 1060A, 2741G, 2741T, 3132C, 3132T, 3387T, 3387C, 3503G, 3503C, 3906G, 3906A.

3. A probe which hybridizes to a polymorphic position as defined in claim 1 at high stringency, wherein high stringency conditions are selected from the goop consisting of hybridization and/or washing at 68° C. in 0.2× SSC and hybridization and/or washing at 42° C. in 50% formamide, 4× SSC.

4. A library of nucleic acids, each of which comprises one or more polymorphic positions within the human ACE gene, wherein said polymorphic positions are selected from the group consisting of positions in the ACE regulatory region (SEQ ID NO: 129) numbered 5106, 5349, and 5496; and positions in the ACE coding region (SEQ ID NO: 130) numbered 375, 582, 731, 1060, 1215, 2193, 2328, 2741, 3132, 3387, 3503, and 3906 and 1451–1783 (SEQ ID NO: 128).

5. A library as defined in claim 4, wherein the sequence at said polymorphic position in the regulatory region is selected from the group consisting of 5106C, 5106T, 5349A, 5349T, 5496T, and 5496C; and the sequence at said polymorphic position in the coding region is selected from the group consisting of 375A, 375C, 582C, 582T, 731A, 731G, 1060G, 1060A, 1215C, 1215T, 2193G, 2193A, 2328A, 2328G, 2741G, 2741T, 3132C, 3132T, 3387T, 3327C, 3503G, 3503C, 3906G, 3906A, and a deletion of nucleotides 1451–1783 (SEQ ID NO: 128).

6. A library of targets for cardiovascular drugs, each of said targets comprising an isolated peptide comprising one or more polymorphic positions in the ACE polypeptide sequence, wherein said polymorphic positions are encoded by nucleotides selected from the group consisting of nucleotide positions in the ACE coding region (SEQ ID NO: 130) numbered 375, 582, 731, 1060, 1215, 2193, 2328, 2741, 3132, 3387, 3503, and 3906.

7. An isolated nucleic acid comprising the human gene encoding angiotensinogen (AGT), wherein said nucleic acid comprises a polymorphic position selected from the group consisting of positions in the regulatory region (SEQ ID NO: 123) numbered 412 and 1072; positions in the coding region (SEQ ID NO:124) numbered 273, 997, and position 49 (SEQ ID NO: 126); and combinations of any of the foregoing.

8. A nucleic acid as defined in claim 7 wherein the sequence at said polymorphic position in the regulatory region is selected from the group consisting of 412C, 412T, 1072C and 1072A; and the sequence at the polymorphic position in the coding region is selected from the group consisting of 273C, 273T, 997G, 997C, and A or G at position 49 (SEQ ID NO: 126).

9. A probe which hybridizes to a polymorphic position as defined in claim 7 at high stringency, wherein high stringency conditions are selected from the group consisting of hybridization and/or washing at 68° C. in 0.2× SSC and hybridization and/or washing at 42° C. in 50% formamide, 4× SSC.

10. A library of nucleic acids, each of which comprises one or more polymorphic positions within the human AGT gene, wherein said polymorphic position is selected from the group consisting of positions in the regulatory region (SEQ ID NO: 123) numbered 395, 412, 432, 449, 692, 839, 1007, 1072, 1204, and 1218; positions in the coding region (SEQ ID NO: 124) numbered 273, 620, 803, 912, 997, 1116, and 1174; and position 49 in the AGT gene (SEQ ID NO: 126).

11. A library as defined in claim 10, wherein the sequence at said polymorphic position in the regulatory region is selected from the group consisting of 395T, 395A, 412C, 412T, 432G, 432A, 449T, 449C, 692C, 692T, 839G, 839A, 1007G, 1007A, 1072G, 1072A, 1204C, 1204A, 121 8A, 1218G; and the sequence at said polymnorphic position in the coding region is selected from the group consisting of 273C, 273T, 620C, 620T, 803T, 803C, 912C, 912T, 997G, 997C, 1116G, 1116A, 1174C, 11 74A, and A or G at position 49 (SEQ ID NO: 126).

12. A library of targets for cardiovascular drugs, each of said targets comprising an isolated peptide comprising one or more polymorphic positions in the AGT polypeptide, wherein said polymorphic positions are encoded by nucleotides selected from the group consisting of nucleotide positions numbered 273, 620, 803, 912, 997, 1116, and 1174 of SEQ ID NO: 124.

13. An isolated nucleic acid comprising the human gene encoding type I angiotensin II receptor (AT1), wherein said nucleic acid comprises a polymorphic position selected from the group consisting of positions in the regulatory region (SEQ ID NO: 131) numbered 1427, 1756, 1853, 2046, 2354, 2355, and 2415; a position in the coding/intron region (SEQ ID NOS: 132–133, which are contiguous) numbered 449; and combinations of the foregoing.

14. A nucleic acid as defined in claim 13 wherein the sequence at said polymorphic position in the regulatory region is selected from the group consisting of 1427A, 1427T, 1756T, 1756A, 1853T, 1853G, 2046T, 2046C, 2354A, 2354C, 2355G, 2355C, 2415A and 2415G; and the sequence at said polymorphic position in the coding/intron region is selected from the group consisting of 449G and 449C.

15. A probe which hybridizes to a polymorphic position as defined in claim 13 at high stringency, wherein high stringency conditions are selected from the group consisting of hybridization and/or washing at 68° C. in 0.2× SSC and hybridization and/or washing at 42° C. in 50% formamide, 4× SSC.

16. A library of nucleic acids, each of which comprises one or more polymorphic positions within the human AT1 gene, wherein said polymorphic position is selected from the group consisting of positions in the regulatory region (SEQ ID NO: 131) numbered 1427, 1756, 1853,2046,2354,2355, and 2415; and positions in the coding region (SEQ ID NOS: 132–133, which are contiguous) numbered 449, 678, 1167, and 1271.

17. A library as defined in claim 16, wherein the sequence at said polymorphic position in the regulatory region is selected from the group consisting of 1427A, 1427T, 1756T, 1756A, 1853T, 1853G, 2046T, 2046C, 2354A, 2354C, 2355G, 2355C, 2415A and 2415G; and the sequence at said polymorphic position in the coding region is selected from the group consisting of 449G, 449C, 678T, 678C, 1167A, 1167G, 1271A, and 1271C.

18. A library of targets for cardiovascular drugs, each of said targets comprising an isolated peptide comprising one or more polymorphic positions in the AT1 polypeptide, wherein said polymorphic positions are encoded by nucleotides selected from the group consisting of nucleotide positions numbered 449, 678, 1167, and 1271 of continuous SEQ ID NOS: 132–133.

19. A library of polymorphic patterns in the human ACE (SEQ ID NOS: 129–130), AGT (SEQ ID NOS: 123–127), and/or AT1 (SEQ ID NO: 132–133, which are contiguous) genes, comprising a member selected from the group consisting of: ACE 5349 A/T, AGR 1218 A; ACE 5496 C, AGR 1204 A/C; ACE 5496 C/T, AGR 1218 A, AGT 620 C/T; ACE 2193 A, AGR 1204 C, ACE 2328 G; ACE 2193 A, AGR 1204 A/C; ACE 3387 T, AGR 1218 A; ACE 3387 T, AGT 620 C/T; AGR 1204 A/C, AT1 678 C/T; AGR 1204 A/C, AT1 1271 A/C; ACE 1215 C, AGR 1204 A/C; AGR 1204 A/C, AT1 1167 A, ACE 3906 A/G; AGR 1204 A, AGT 620 C, AT1 1271 A, AT1 1167 A, AGR 395 A/T; AGR 1204 A/C, AGT 620 C/T, AT1 1271 A/C, AT1 1167 A, AGR 395 T; AGR 1204 A/C, AGT 620 C/T, AT1 1271 A/C, AT1 1167 A/G, AGR 395 T; AGR 1204 A, AT1 678 C, AT1 1167 A, AGR 395 A/T; AGR 1204 A/C, AT1 678 C/T, AT1 1167 A, AGR 395 T; AGT 620 C/T, AT1 1271 A/C, AT1 1167 A, AGR 395 T; AGT 620 C/T, AT1 1271 A/C, AT1 1167 A/G, AGR 395 T; AGT 620 C, AT1 1271 A, AT1 1167 A, AGR 395 A/T, AGT 620 C, AT1 678 A, AT1 1167 A, AGR 395 A/T; AGT 620 C/T, AT1 678 C/T, AT1 1167 A, AGR 395 T; ACE 2193 A, AGR 1218 A, AGT 803 A; ACE 2193 A, AGT 620 C/T; ACE 2328 G, AGT 620 C/T; ACE 3387 T, AGR 1204 A/C; ACE 2193 A, ACE 2328 G, AGR 1204 C; and ACE 2193 A/G, AGR 1072 G/A, AT1 1167 A/G.

20. A kit for assessing responsiveness of an individual to a treatment regimen of a cardiovascular syndrome, said kit comprising
(i) sequence determination primers and
(ii) sequence determination reagents,
wherein said primers are selected from the group consisting of primers that hybridize to polymorphic positions in human ACE, AGT, or AT1 genes; and primers that hybridize immediately adjacent to polymorphic positions in human ACE, AGT, or AT1 genes, wherein said polymorphic positions are selected from the group consisting of positions in the ACE regulatory region (SEQ ID NO: 129) numbered 5106, 5349, and 5496; positions in the ACE coding region (SEQ ID NO: 131) numbered 375, 582, 731, 1060, 1215, 2193, 2328, 2741, 3132, 3387, 3503, and 3906; positions in the AGT regulator region (SEQ ID NO: 123) numbered 395, 412, 432, 449, 692, 839, 1007, 1072, 1204 and 1218; positions in tie AGT coding region (SEQ ID NO: 124) numbered 273, 620, 803, 912, 997, 1116, and 1174; position 49 in the AGT gene (SEC ID NO; 126) position 1451 in the ACE gene (SEQ ID NO: 128); positions in the AT1 regulatory region numbered 1427, 1756, 1853, 2046, 2354, 2355, and 2415; positions in the AT1 coding region (SEQ ID NOS: 132–133, which are contiguous) numbered 449, 678, 1167, and 1271; and combinations of any of the foregoing.

21. A kit for assessing cardiovascular status, said kit comprising one or more antibodies specific for a polymorphic position within the human ACE, AGT, or AT1 polypeptides.

22. A kit as defined in claim 21, wherein said polymorphic positions are encoded by a nucleotide selected from the group consisting of nucleotide positions in the ACE coding region (SEQ ID NO: 130) numbered 375, 582, 731, 1060, 1215, 2193, 2328, 2741, 3132, 3387, 3503, and 3906; nucleotide positions in the AGT coding region (SEQ ID NO: 124) numbered 273, 620, 803, 912, 997, 1116, and 1114; positions in the AT1 coding region (SEQ ID NOS: 132–133 which are contiguous) numbered 449, 678, 1167, and 1271; and combinations of any of the foregoing.

23. A method for predicting the response of a human individual having a cardiovascular syndrome to a treatment regimen of said cardiovascular syndrome, which method comprises comparing a polymorphic pattern established in one or more polymorphic positions within one or more of the ACE, AGT, or AT1 genes of said individual wit a polymorphic pattern of the same polymorphic positions of humans who have a known response to the treatment regimen.

24. A method as defined in claim 23, wherein said treatment regimen is an alteration in diet, lifestyle, and/or exercise; a surgical technique, or a pharmaceutical intervention.

25. A method as defined in claim 24, wherein said treatment regimen is a pharmaceutical intervention.

26. A method as defined in claim 25, wherein said treatment regimen comprises administering a cardiovascular drug selected from the group consisting of ACE inhibitors, angiotensin II receptor antagonists, diuretics, alpha-adrenoreceptor antagonists, cardiac glycosides, phosphodiesterase inhibitors, beta-adrenoreceptor antagonists, calcium channel blockers, HMG-CoA reductase inhibitors, imidizoline receptor blockers endothelin receptor blockers, and organic nitrites.

27. A method as defined in claim 26, wherein said polymorphic positions comprise ACE 2193 (SEQ ID NO: 130), AGT 1072 (SEQ ID NO: 123), and AT1 1167 (SEQ ID NOS. 132–133 which are contiguous).

28. A method as defined in claim 27, wherein said polymorphic pattern comprises ACE 2193 A/G, AGT 1072 G/A, and AT1 1167 A/G.

29. A method as defined in claim 23, wherein said cardiovascular syndrome is selected from the group consisting of myocardial infarction, hypertension, atherosclerosis, and stroke.

30. A method as defined in claim 23, wherein said treatment regimen is the administration of an ACE inhibitor, wherein said method comprises comparing the polymorphic pattern established by determining the sequence of (a) the ACE gene (SEQ ID NO: 130) at position 2193 in the coding region; (b) the AGT gene (SEQ ID NO: 123) at position 1072 in the regulatory region; and (c) the AT gene (SEQ ID NOS: 132–133, which are contiguous) at position 1167 in the coding region with the same polymorphic patterns of humans exhibiting different responses to said ACE inhibitor.

31. A method as defined in claim 30, wherein said polymorphic pattern comprises ACE 2193 A/G, AGT 1072 G/A, AT 1 1167 A/G.

32. A method for assessing cardiovascular status in a human individual, which method comprises comparing a polymorphic pattern established in one or more polymorphic positions within one or more of the ACE, AGT, or AT1 genes of said individual with a polymorphic pattern of the same polymorphic positions of humans who have a known cardiovascular status, wherein said polymorphic positions comprise ACE 2193 of SEQ ID NO: 130, AGT 1072 of SEQ ID NO: 123, and AT1 1167 (SEQ ID NOS: 132–133, which are contiguous).

33. A method as defined in claim 32, wherein said polymorphic pattern comprises ACE 2193 A/G, AGT 1072 G/A, and AT1 1167 A/G.

34. A method as defined in claim 32, which method comprises comparing the polymorphic pattern established by determining the sequence of (a) the ACE gene at position 2193 in the coding region; (b) the AGT gene at position 1072 in the regulatory region; and (c) the AT1 gene at position 1167 in the coding region.

35. A method as defined in claim 34, wherein said polymorphic pattern comprises ACE 2193 A/G, AGR 1072 G/A, AT1 1167 A/G.

36. A method for assessing cardiovascular status in a human individual, which method comprises comparing a polymorphic pattern established in one or more polymorphic positions within one or more of the ACE, AGT, or AT1 genes of said individual with a polymorphic pattern of the same polymorphic positions of humans who have a known cardiovascular status, wherein said polymorphic position is selected from the group consisting of positions in the ACE regulatory region (SEQ ID NO:129) numbered 5106, 5349, and 5496; positions in the ACE coding region (SEQ ID NO:130) numbered 375, 582, 731, 1060, 1215, 2193, 2328, 2741, 3132, 3387, 3503, and 3906; positions in the AGT regulatory region (SEQ ID NO: 123) numbered 395, 412, 432, 449, 692, 839, 1007, 1072, 1204, and 1218; positions in the AGT coding region (SEQ ID NO: 124) numbered 273, 620, 803, 912, 997, 1116, and 1174; position 49 in the AGT gene (SEQ ID NO:126); position 1451 in the ACE gene (SEQ ID NO:128); positions in the AT1 regulatory region (SEQ ID NO:131) numbered 1427, 1756, 1853, 2046, 2354, 2355, and 2415; positions in the AT1 coding region (SEQ ID NOS:132–133, which are contiguous) numbered 449, 678, 1167, and 1271; and combinations of any of the foregoing.

37. A method as defined in claim 36, wherein said polymorphic patterns are selected from the group consisting of: ACE 5349 A/T, AGR 1218 A; ACE 5496 C, AGR 1204 A/C; ACE 5496 C/T, AGR 1218 A, AGT 620 C/T; ACE 2193 A, AGR 1204 C, ACE 2328 G; ACE 2193 A, AGR 1204 A/C; ACE 3387 T, AGR 1218 A; ACE 3387 T, AGT 620 C/T; AGR 1204 A/C, AT1 678 C/T; AGR 1204 A/C, AT1 1271 A/C; ACE 1215 C, AGR 1204 A/C; AGR 1204 A/C, AT1 1167 A, ACE 3906 A/G; AGR 1204 A, AGT 620 C, AT1 1271 A, AT1 1167 A, AGR 395 A/T; AGR 1204 A/C, AGT 620 C/T, AT1 1271 A/C, AT1 1167 A, AGR 395 T; AGR 1204 A/C, AGT 620 C/T, AT1 1271 A/C, AT1 1167 A/G, AGR 395 T; AGR 1204 A, AT1 678 C, AT1 1167 A, AGR 395 A/T; AGR 1204 A/C, AT1 678 C/T, AT1 1167 A, AGR 395 T; AGT 620 C/T, AT1 1271 A/C, AT1 1167 A, AGR 395 T; AGT 620 C/T, AT1 1271 A/C, AT1 1167 A/G AGR 395 T; AGT 620 C, AT1 1271 A, AT1 1167 A, AGR 395 A/T; AGT 620 C, AT1 678 A, AT1 1167 A, AGR 395 A/T; AGT 620 C/T, AT1 678 C/T; AT1 1167 A, AGR 395 T; ACE 2193 A, AGR 1218 A, AGT 803 A; ACE 2193 A, AGT 620 C/T; ACE 2328 G, AGT 620 C/T; ACE 3387 T, AGR 1204 A/C; ACE 2193 A, ACE 2328 G, AGR 1204 C; and ACE 2193 A/G, AGR 1072 G/A, AT1 1167 A/C.

38. A method for predicting the response of a human individual having a cardiovascular syndrome to a treatment regimen of said cardiovascular syndrome, which method comprises comparing a polymorphic pattern established in a combination of polymorphic positions within one or more of the ACE, AGT, or AT1 genes of said individual with a polymorphic pattern of the same polymorphic positions of humans who heave a known response to the treatment regimen.

39. A method as defined in claim 23, wherein said polymorphic position is selected from the group consisting of positions in the ACE regulatory region (SEQ ID NO: 129) numbered 5106, 5349, and 5496; positions in the ACE coding region (SEQ ID NO: 130) numbered 375, 582, 731, 1060, 1215, 2193, 2328, 2741, 3132, 3387, 3503, and 3906; positions in the AGT regulatory region (SEQ ID NO: 123) numbered 395, 412, 432, 449, 692, 839, 1007, 1072, 1204, and 1218; positions in the AGT coding region (SEQ ID NO: 124) numbered 273, 620, 803, 912, 997, 1116, and 1174; position 49 in the AGT gene (SEQ ID NO: 126); position 1451 in the ACE gene (SEQ ID NO: 128); positions in the AT1 regulatory region (SEQ ID NO: 131) numbered 1427, 1756, 1853, 2046, 2354, 2355, and 2415; positions in the AT1 coding region (SEQ ID NO: 132–133, which are contiguous) numbered 449, 678, 1167, and 1271; and combinations of any of the foregoing.

40. A method as defined in claim 39, wherein said polymorphic patterns are selected from the group consisting of: ACE 5349 A/T, AGR 1218 A; ACE 5496 C, AGR 1204 A/C; ACE 5496 C/T, AGR 1218 A, AGT 620 C/T; ACE 2193 A, AGR 1204 C, ACE 2328 G; ACE 2193 A, AGR 1204 A/C; ACE 3387 T, AGR 1218 A; ACE 3387 T, AGT 620 C/T; AGR 1204 A/C, AT1 678 C/T; AGR 1204 A/C, AT1 1271 A/C; ACE 1215 C, AGR 1204 A/C, AGR 1204 A/C, AT1 1167 A, ACE 3906 A/G; AGR 1204 A, AGT 620 C, AT1 1271 A, AT1 1167 A, AGR 395 A/T; AGR 1204 A/C, AGT 620 C/T, AT1 1271 A/C, AT1 1167 A, AGR 395 T; AGR 1204 A/C, AGT 620 C/T, AT1 1271 A/C, AT1 1167 A/G, AGR 395 T; AGR 1204 A, AT1 678 C, AT1 1167 A, AGR 395 A/T; AGR 1204 A/C, AT1 678 C/T, AT1 1167 A, AGR 395 T; AGT 620 C/T, AT1 1271 A/C, AT1 1167 A, AGR 395 T; AGT 620 C/T, AT1 1271 A/C, AT1 1167 A/G, AGR 395 T; AGT 620 C, AT1 1271 A, AT1 1167 A, AGR 395 A/T; AGT 620 C, AT1 678 A, AT1 1167 A, AGR 395 A/T; AGT 620 C/T, AT1 678 C/T; AT1 1167 A, AGR 395 T; ACE 2193 A, AGR 1218 A, AGT 803 A; ACE 2193 A, AGT 620 C/T; ACE 2328 G, AGT 620 C/T; ACE 3387 T, AGR 1204 A/C; ACE 2193 A, ACE 2328 G, AGR 1204 C; and ACE 2193 A/G, AGR 1072 G/A, AT1 1167 A/G.

* * * * *

SEQUENCE LISTING

<160> NUMBER OF SEQ ID NOS: 133

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 1
tgcgtgcttc agaagtcc                                                18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 2
ccagggaggt gaagaaatc                                               19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 3
agccaggcag taatgacct                                               19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 4
gcccactgtt cccttatg                                                18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 5
tgccctgact gacagagc                                                18

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: PCR PRIMER

<400> SEQUENCE: 6
gccctggtgt gcctgt                                                  16

<210> SEQ ID NO 7
<211> LENGTH: 18

```
<212> TYPE: DNA
<213> ORGANISM: Artificial Sequence
<220> FEATURE:
<223> OTHER INFORMATION: Description of Artificial Sequence: PCR PRIMER

<400> SEQUENCE: 7
tgcctggata tgtgttgc                                               18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 8
tgcctggata tgtgttgc                                               18

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: PCR PRIMER

<400> SEQUENCE: 9
gccctcgcct ctcact                                                 16

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 10 tccctctcc ctgtacct                                                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 11
gtgctggggt agggtaga                                               18

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: PCR PRIMER

<400> SEQUENCE: 12 tcccctgac ctggct                                                  16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: PCR PRIMER

<400> SEQUENCE: 13
```

-continued ggggcaccgt gatgtt                                      16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: PCR PRIMER

<400> SEQUENCE: 14
ggggcaccgt gatgtt                                      16

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 15
gccagagcct ttggttt                                     17

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 16
tggaagagcc gacttacag                                   19

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 17
tcccagaggc aaagagg                                     17

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 18
gtttctactg cggcttcat                                   19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 19
gtttctactg cggcttcat                                   19

<210> SEQ ID NO 20
<211> LENGTH: 19
<212> TYPE: DNA
<213> ORGANISM: Artificial Sequence

```
<220> FEATURE:
<223> OTHER INFORMATION: Description of Artificial Sequence: PCR PRIMER

<400> SEQUENCE: 20
tcctggaaga gggagtttc                                                    19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 21
gcaggatgag agcaacaac                                                    19

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: PCR PRIMER

<400> SEQUENCE: 22
ctggagacca ctcccatcct ttct                                              24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 23
gatgtggcca tcacattcgt cagat                                             25

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 24
cttccgtggg actcatgt                                                     18

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 25
tgcaccgtga ggctcta                                                      17

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 26
gcccaatagg aggaagca                                                     18
```

-continued

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 27
cccaccccat ctccaagaa                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 28
tccctgatgg gctgctctc                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 29
caaggccctc aaccaactc                                                19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 30
ttcccacaaa agctccagtg                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 31
ggctcaaaat ggcaagtgtt                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 32
gggccatgtc cttctgactc                                               20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 33
cagcctggag gggttaaga                                                        19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 34
cccttctgag cgagctgagt                                                       20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 35
ggccatgttg agctacttca a                                                     21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 36
cctccagcct tgggtcttaa                                                       20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 37
ttcccatccc agtctctggt                                                       20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 38
ggcagcctgg ttgatgagt                                                        19

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 39
attccagctc tgaaattctc tga                                                   23

<210> SEQ ID NO 40

```
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 40
gagcccctcc agcacctc                                                 18

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 41
acccgagcct gcccacc                                                  17

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 42
ggtcgggctg ggaagatc                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 43
tcggctctgc cccttctc                                                 18

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 44
gccctttctc cagcttcctc t                                             21

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 45
cggcggcagc agcaaca                                                  17

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 46
```

```
gagcccctcc agcacctc                                          18

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 47
acccgagcct gcccacc                                           17

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 48
ggtcgggctg ggaagatc                                          18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 49
tcggctctgc cccttctc                                          18

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 50
gccctttctc cagcttcctc t                                      21

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 51
cggcggcagc agcaaca                                           17

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 52
atggcactta aaggtcagtt aat                                    23

<210> SEQ ID NO 53
<211> LENGTH: 19
<212> TYPE: DNA
```

<213> ORGANISM: Artificial Sequence
<220> FEATURE:
<223> OTHER INFORMATION: Description of Artificial Sequence: PCR PRIMER

<400> SEQUENCE: 53
tacggaagcc caagaagtt                                                19

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 54
ctccccaacg gctgtctt                                                 18

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 55
agcagcaaca tccagttctg t                                             21

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 56
tcccacgctc tctggactt                                                19

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: PCR PRIMER

<400> SEQUENCE: 57
ctgatctcag ctacacatgg atacta                                        26

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 58
cctgtcttgg gtgactcttc                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 59
ttctgggcta aatggtgaca                                               20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 60
cttgtcttcg gtgtcaagtt t                    21

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 61
gggagccttg gaccacac                        18

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 62
agcctgcatg aacctgtcaa                      20

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 63
tggtgggcgt gttcaca                         17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 64
gccagagcca gcagaga                         17

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 65
ccacattcca ggggagac                        18

<210> SEQ ID NO 66
<211> LENGTH: 20
<212> TYPE: DNA
<213> ORGANISM: Artificial Sequence
<220> FEATURE:

<223> OTHER INFORMATION: Description of Artificial Sequence: PCR PRIMER

<400> SEQUENCE: 66
cctgtcttgg gtgactcttc                                    20

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 67
ccacattcca ggggagac                                      18

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 68
gtcccttcag tgccctaata c                                  21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 69
acagccagat tgaaagacac a                                  21

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 70 aacccttta ctggtcatgt ga                                  22

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 71
cgctcatggg atgtgtgac                                     19

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 72
tgttttcccc agtgtctatt aga                                23

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 73
gcagggtcga gttacacatt t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 74
cctcaggctg tcacacacct a                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 75
cggcttacct tctgctgtag t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 76
ctccttgaac ctgcttgtgt t                                              21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 77
gcattgaaag atgtgctgtt ct                                             22

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 78
taacgactac aaaagcaagt cttac                                          25

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 79
agagggcagg ggagagtct                                              19

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 80
ggcagcaggg tcagaagt                                               18

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 81
gctggagagg agggttacat                                             20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 82
tgcaaacttc ggtaaatgtg t                                           21

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 83
cagaacaacg gcagcttct                                              19

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: PCR PRIMER

<400> SEQUENCE: 84
actggctgac ttatgctttt tact                                        24

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 85
gggttgaatt ttgggactca ta                                          22

<210> SEQ ID NO 86
<211> LENGTH: 20

```
<212> TYPE: DNA
<213> ORGANISM: Artificial Sequence
<220> FEATURE:
<223> OTHER INFORMATION: Description of Artificial Sequence: PCR PRIMER

<400> SEQUENCE: 86
gccagtttgc cagctataat                                                 20

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 87
tgatgcctag ttgaatcaat aca                                             23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 88
gaaggcttat gaaattcaga aga                                             23

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 89
aaagtcggtt cagtccacat aa                                              22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 90
aaacagcttg gtggtgatag tc                                              22

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 91
gcaggtgact ttggctacaa                                                 20

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: PCR PRIMER

<400> SEQUENCE: 92
```
cctgtacgct agtgtgtttc tact                                    24

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 93
aggaaacagg aaacccagta tat                                     23

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 94
ctggattccc caccaaatat                                         20

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 95
tgctccttct ttcacaaaat tac                                     23

<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence: PCR PRIMER

<400> SEQUENCE: 96
cttccgttat tatgtgtgat attagt                                  26

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 97
gcatgtacct aaaaagtcct gtc                                     23

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 98
attggcatat ccatcacctt aa                                      22

<210> SEQ ID NO 99
<211> LENGTH: 22
<212> TYPE: DNA
<213> ORGANISM: Artificial Sequence -continued

```
<220> FEATURE:
<223> OTHER INFORMATION: Description of Artificial Sequence: PCR PRIMER

<400> SEQUENCE: 99
gatctcccaa ctcatgctat ga                                               22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 100
attggattca atttgcctac at                                               22

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 101
tttggtaata cagttgtgga tcata                                            25

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: PCR PRIMER

<400> SEQUENCE: 102
tgcaacttgg gtagcatgtc                                                  20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 103
agtcgtcccg tgtcaactat c                                                21

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 104
cgttgtcttc cgttattatg tgt                                              23

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 105
ttattgcatg tacctaaaaa gtgta                                            25
```

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 106
gcattcatat aaagatcaaa tcagt                                      25

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: PCR PRIMER

<400> SEQUENCE: 107
caccctgata acaaaaccag ata                                        23

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 108
ctttctggca tcaacctcac t                                          21

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: PCR PRIMER

<400> SEQUENCE: 109
acttttaagg acgaattaga gaact                                      25

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 110
gtccaccctt gaatttcata ac                                         22

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 111
cccaacctcc tccctctc                                              18

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: PCR PRIMER

```
<400> SEQUENCE: 112
gctcgctctc cctcacgac                                               19

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 113
tccagccgct ccccatc                                                 17

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: PCR PRIMER

<400> SEQUENCE: 114
gctcgctctc cctcacgac                                               19

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: PCR PRIMER

<400> SEQUENCE: 115
tccagccgct ccccatc                                                 17

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 116
gcccctcaga taatgtaagc tc                                           22

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: PCR PRIMER

<400> SEQUENCE: 117
aaccggcacg aaaactttac t                                            21

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 118
gcacttcact accaaatgag ca                                           22

<210> SEQ ID NO 119
```

```
<211> LENGTH: 22
<212> TYPE: DNA
<213> ORGANISM: Artificial Sequence
<220> FEATURE:
<223> OTHER INFORMATION: Description of Artificial Sequence: PCR PRIMER

<400> SEQUENCE: 119
gcacttcact accaaatgag cc                                              22

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: PCR PRIMER

<400> SEQUENCE: 120
caggaaacag ctatgact                                                   18

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: PCR PRIMER

<400> SEQUENCE: 121
agtcacgacg ttgtaaaacg acggccagt                                       29

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: PCR PRIMER

<400> SEQUENCE: 122
cgacgttgta aaacgacggc cagt                                            24

<210> SEQ ID NO 123
<211> LENGTH: 1278
<212> TYPE: DNA
<213> ORGANISM: Homo sapiens
<220> FEATURE:
<223> OTHER INFORMATION: Angiotensinogen, 5' region and exon 1

<400> SEQUENCE: 123
ccagacaagt gatttttgag gagtccctat ctataggaac aaagtaatta aaaaaatgta     60
tttcagaatt tacaggccca tgtgagatat gatttttta aatgaagatt tagagtaatg    120
ggtaaaaaag aggtatttgt gtgtttgttg attgttcagt cagtgaatgt acagcttctg   180
cctcatatcc aggcaccatc tcttcctgct ctttgttgtt aaatgttcca ttcctgggta   240
atttcatgtc tgccatcgtg gatatgccgt ggctccttga acctgcttgt gttgaagcag   300
gatcttcctt cctgtcccct cagtgcccta ataccatgta tttaaggctg gacacatcac   360
cactcccaac ctgcctcacc cactgcgtca cttgtgatca ctggcttctg gcgactctca   420
ccaaggtctc tgtcatgccc tgttataacg actacaaaag caagtcttac ctataggaaa   480
ataagaatta taacccttttt actggtcatg tgaaacttac catttgcaat ttgtacagca   540
taaacacaga acagcacatc tttcaatgcc tgcatcctga aggcattttg tttgtgtctt   600
tcaatctggc tgtgctattg ttggtgttta acagtctccc cagctacact ggaaacttcc   660
agaaggcact tttcacttgc ttgtgtgttt tccccagtgt ctattagagg cctttgcaca   720
```

```
gggtaggctc tttggagcag ctgaaggtca cacatcccat gagcgggcag cagggtcaga    780
agtggccccc gtgttgccta agcaagactc tcccctgccc tctgccctct gcacctccgg    840
cctgcatgtc cctgtggcct cttggggggta catctcccgg ggctgggtca gaaggcctgg   900
gtggttggcc tcaggctgtc acacacctag ggagatgctc ccgtttctgg gaaccttggc    960
cccgactcct gcaaacttcg gtaaatgtgt aactcgaccc tgcaccggct cactctgttc   1020
agcagtgaaa ctctgcatcg atcactaaga cttcctggaa gaggtcccag cgtgagtgtc   1080
gcttctggca tctgtccttc tggccagcct gtggtctggc caagtgatgt aaccctcctc   1140
tccagcctgt gcacaggcag cctgggaaca gctccatccc caccctcag ctataaatag     1200 ggcctcgtga cccggccagg ggaagaagct gccgttgttc tgggtactac agcagaaggt   1260
aagccggggg ccccctca                                                 1278
```

<210> SEQ ID NO 124
<211> LENGTH: 1347
<212> TYPE: DNA
<213> ORGANISM: Homo sapiens
<220> FEATURE:
<223> OTHER INFORMATION: Angiotensinogen, exon 2

<400> SEQUENCE: 124

```
gtccatctcc tcatctcctc ttctcataag gacacaggtc atattagatc agggctcacc    60
ctcatggcct cattttaact taatcatctc tttaaagatc ctgtctccaa ataatggtca   120
cattctaggt cctggggttt aggacttcaa cacgggcatt atggccgttg gggaggtagg   180
acataattca gctgatattg tgcattttgc acttggatca tgtagatatt ttccatggag   240
ctttgaatcc atttcttctt ttttttgtag acatgaatga tttattctgg gctaaatggt   300
gacaggaata ttgagacaat gaaagatctg gttagatggc acttaaaggt cagttaataa   360
ccacctttca ccctttgcaa aatgatattt caggtatgcg gaagcgagca ccccagtctg   420
agatggctcc tgccggtgtg agcctgaggg ccaccatcct ctgcctcctg gcctgggctg   480
gcctggctgc aggtgaccgg gtgtacatac accccttcca cctcgtcatc cacaatgaga   540
gtacctgtga gcagctggca aaggccaatg ccgggaagcc caaagacccc accttcatac   600
ctgctccaat tcaggccaag acatcccctg tggatgaaaa ggccctacag gaccagctgg   660
tgctagtcgc tgcaaaactt gacaccgaag acaagttgag ggccgcaatg gtcgggatgc   720
tggccaactt ctttgggcttc cgtatatatg gcatgcacag tgagctatgg ggcgtggtcc   780
atggggccac cgtcctctcc ccaacggctg tctttggcac cctggcctct ctctatctgg   840
gagccttgga ccacacagct gacaggctac aggcaatcct gggtgttcct tggaaggaca   900
agaactgcac ctcccggctg gatgcgcaca aggtcctgtc tgccctgcag ctgtacagg    960 gcctgctagt ggcccagggc agggctgata gccaggccca gctgctgctg tccacggtgg   1020
tgggcgtgtt cacagcccca ggcctgcacc tgaagcagcc gtttgtgcag ggcctggctc   1080
tctatacccc tgtggtcctc ccacgctctc tggacttcac agaactggat gttgctgctg   1140
agaagattga caggttcatg caggctgtga caggatggaa gactggctgc tccctgatgg   1200
gagccagtgt ggacagcacc ctggctttca cacctacgt ccacttccaa ggtaaggcaa    1260
acctctctgc tggctctggc cctaggactt agtatccatg tgtagctgag atcagccagt   1320
caggccttgg agatgggcag ggggcag                                      1347
```

<210> SEQ ID NO 125

```
<211> LENGTH: 377
<212> TYPE: DNA
<213> ORGANISM: Homo sapiens
<220> FEATURE:
<223> OTHER INFORMATION: Angiotensinogen, exon 3

<400> SEQUENCE: 125 cctgccctg tcttgggtga ctcttccctc cctgtctcct gtctgatttc agggaagatg      60
aagggcttct ccctgctggc cgagcccag gagttctggg tggacaacag cacctcagtg    120
tctgttccca tgctctctgg catgggcacc ttccagcact ggagtgacat ccaggacaac    180
ttctcggtga ctgaagtgcc cttcactgag agcgcctgcc tgctgctgat ccagcctcac    240
tatgcctctg acctggacaa ggtggagggt ctcactttcc agcaaaactc cctcaactgg    300
atgaagaaac tgtctccccg gtagagccct cccggtctcc cctggaatgt gggagccaca    360
ctctcctgac ccaggct                                                   377

<210> SEQ ID NO 126
<211> LENGTH: 273
<212> TYPE: DNA
<213> ORGANISM: Homo sapiens
<220> FEATURE:
<223> OTHER INFORMATION: Angiotensinogen, exon 4

<400> SEQUENCE: 126
cctctgggag agccctcact gtgtggcctg gagccttcct aactgtgcat catctcccca     60
ggaccatcca cctgaccatg ccccaactgg tgctgcaagg atcttatgac ctgcaggacc    120
tgctcgccca ggctgagctg cccgccattc tgcacaccga gctgaacctg caaaaattga    180
gcaatgaccg catcagggtg ggggaggtat ttaccttcct tgcctacctg gtccattgca    240
caggtgagca tgattaagga aaagagctat ggt                                 273

<210> SEQ ID NO 127
<211> LENGTH: 945
<212> TYPE: DNA
<213> ORGANISM: Homo sapiens
<220> FEATURE:
<223> OTHER INFORMATION: Angiotensinogen, exon 5

<400> SEQUENCE: 127
agcccaccgc cggccctcta gccctcacga ccctgggtca cccatgcgcc ctcagaatga     60
tcctgatcct gatgtctggt cctttgcagg tgctgaacag cattttttt gagcttgaag    120 cggatgagag agagcccaca gagtctaccc aacagcttaa caagcctgag gtcttggagg    180
tgaccctgaa ccgccattc ctgtttgctg tgtatgatca aagcgccact gcctgcact    240 tcctgggccg cgtggccaac ccgctgagca cagcatgagg ccagggcccc agaacacagt    300
gcctggcaag gcctctgccc ctggcctttg aggcaaaggc cagcagcaga taacaacccc    360
ggacaaatca gcgatgtgtc accccagtc tcccaccttt tcttctaatg agtcgacttt    420
gagctggaaa gcagccgttt ctccttggtc taagtgtgct gcatggagtg agcagtagaa    480
gcctgcagcg gcacaaatgc acctcccagt ttgctgggtt tattttagag aatgggggtg    540
gggaggcaag aaccagtgtt tagcgcggga ctactgttcc aaaaagaatt ccaaccgacc    600
agcttgtttg tgaaacaaaa aagtgttccc ttttcaagtt gagaacaaaa attgggtttt    660
aaaattaaag tatacatttt tgcattgcct tcggtttgta tttagtgtct tgaatgtaag    720
aacatgacct ccgtgtagtg tctgtaatac cttagttttt tccacagatg cttgtgattt    780
ttgaacaata cgtgaaagat gcaagcacct gaatttctgt ttgaatgcgg aacaatagct    840
```

```
ggttatttct cccttgtgtt agtaataaac gtcttgccac actaagcctc caaatttact    900
ctttattaga cgccaacaga tgtatacatt cagccagata gactg                    945
```

<210> SEQ ID NO 128
<211> LENGTH: 1856
<212> TYPE: DNA
<213> ORGANISM: Homo sapiens
<220> FEATURE:
<223> OTHER INFORMATION: Angiotensin I converting enzyme, intron 16

<400> SEQUENCE: 128

```
gtgagagctc atgtgcaggc tgagtgagag gcgagggctg ggactggcat ggggcccggg     60
ggtgctgggt gagagcacag agttgggctc ccctcgctct tggggtcagc gtgcccagga    120
aatgcccttt cttgttttcc acgagggggg cttctctgcc cactgagagc cggcacctac    180
ttcataccat gccccgatca gctgcccctc cctcagaacc gccctctgct taagggtgtc    240
cactctctcc tgtcctctct gcatgccgcc cctcagagca gcgggatctc aaagttatat    300
ttcatgggct tggactccaa atgggggaa ctcggggaca ctagctcccc ccggcctcct     360
ttcgtgaccc tgcccttgac ttcctcacct tctctgtctt tcctgagccc ctctcccagc    420
atgtgactga taaggaaatt gagtcacaca gcccctgaaa gcgccagact agaacctgag    480
cctctgattc ctctcacttc cctccctac cctgccactt cctactggat agaagtagac     540
agctcttgac tgtcctctt tctccccact ggctggtcct tcttagcccc agcccgtttg     600
aaagagctca ccccgacac aaggacccgc acacagatac ctcccagctc cctctcaacc     660
cacccttttc agggttggag aacttgaggc ataaacattc ttccatgagg aatctccacc    720
cagaaatggg tctttctggc ccccagccca gctcccacat tagaacaatg acaaatagaa    780
ggggaaatgg aaaataaaca ggagaaacgg ttttcccagg acagggtttg gcctacaagt    840
tgtggatgtg ggtacccatg ccaagtgtga ggggaggctg gccgggtgtg gtggctcatg    900
ctctaatccc agcactttgg gaggccaagg tgagtagatc acttgaggcc gggagtttga    960
gaccagcctg gccaacatgg tgaaacccca tctgtactaa aaatacaaaa gttagctggg   1020
cgtggtggta gatgcctgta gtcccagcta cttgggaggc tgaggcatga gaatcgcttg   1080
agcccagcca gggcaataca gcaagacccc gtctctacaa ataaaataca aaaattagt    1140 tggatgtggt ggtgcatgcc tgtagtccta gctgctaggg aggctgagat ggaaggattg   1200
cttgagcctg ggaggtcaag gctgcagtga gccgagatgg cgccactgca ctccagcctg   1260
ggcaacagag tgagaccctg tctcagaaag aaaaaaaaaa aaaaggaga ggagagagac    1320 tcaagcacgc ccctcacagg actgctgagg ccctgcaggt gtctgcagca tgtgcccagg   1380
ccggggactc tgtaagccac tgctggagac cactcccatc ctttctccca tttctctaga   1440
cctgctgcct atacagtcac ttttttttt ttttgagac ggagtctcgc tctgtcgccc     1500
aggctggagt gcagtggcgg gatctcggct cactgcaacg tccgcctccc gggttcacgc   1560
cattctcctg cctcagcctc ccaagtagct gggaccacag cgcccgccac tacgcccggc   1620
taattttttg tattttttagt agagacgggg tttcaccgtt ttagccggga tggtctcgat   1680
ctcctgacct cgtgatccgc ccgcctcggc ctcccaaagt gctgggatta caggcgtgat   1740
acagtcactt ttatgtggtt tcgccaattt tattccagct ctgaaattct ctgagctccc   1800
cttacaagca gaggtgagct aagggctgga gctcaagcca ttcaacccc taccag        1856
```

<210> SEQ ID NO 129

<211> LENGTH: 5590
<212> TYPE: DNA
<213> ORGANISM: Homo sapiens
<220> FEATURE:
<223> OTHER INFORMATION: Angiotensin I converting enzyme, 5' region

<400> SEQUENCE: 129

```
cagcgttgta caaccatcac tactaatgtc agaacatttc actaccccta aaagaaaccc      60
cataccacag attccgatgc cgccgggagc cctgtcatgc catgtcacat atattatagt     120
atatatatgc ccagccatgg tcaacccacc gtgttctttg acatcaccat caacagcaag     180
cccttgggcc acgtctcctt caagctgttt gcagacaagt ttccaaagac ggcagaaaac     240
tttcctgctc tgagcactgg agagaaaggg tttggttata agagttcctg ctttcacaga     300
attattccag ggtttatgtg tcagggtggt gacttcacac accataatgg cactggtgtc     360
aagtccatct atgggagaa atttgatgat gagaacttca ttctgaagca tacaggtcct     420
ggcatctttt ccatggcaaa tgctggaccc aacacaaatg gttcccagtt ttgcaactgc     480
actgccaaga ctgcgtggtt ggatggcatg catgtggtcc ttggccaagt gaaagaaggc     540
atggatattg cggaggctat ggagcgcttt gggtccagga atggcaagac cagcaagaag     600
attaccattg ccgactgtgg acaactctac taagtttgac ttgtgtttta tcttaaccac     660
cagatcattc cttttgtagc tcaggagagc accctccacc tcatttgctc accgtagcct     720
ctaatctttg tgccatctct cagttccctt tgggttccat gtttgcctta ttctcctcca     780
tgcctagctg gatttcagag ttaagtttat gattatgaga taaaaactaa ataacaattg     840
caaaaaaata aaataaaaag aaagaagagg ctgggagcgg tggctcactc ctctaatccc     900
agcactttgg gaggccgagg tgggcctacc aaaggtcagg agatcgagac caccctggct     960
aacacggtga atcccatgt ctactaaaaa tacaaaaaaa attagccagg cgtcgtggcg    1020
tgcctgcggt cccagctact cggaaggctg aggcagagga atggcgtgaa cccaggaggt    1080
ggagcttgca gtgagccgag atcgcaccac tgcactccag cctgggcaac agagcaagac    1140
tctatctcaa aaaaaaaaaa aaaaaagac ggaaaggca ttatatattt gtgaagacat    1200
ggacagaaat gtgtcctgat tgtggtgcca caaagcactg agcctactag aagacgtcag    1260
caaaagatcc cctgaaaagt gactccaagc cattcactgc aagggatggt tacacagatg    1320
cagaatacag aaggtcaata gtagcttaat gctacatcac agcttaacac tacatcatcc    1380
acctcacttc atctcacccc atcgtatcgt gtcactgtgc tcaccatcac aagaacaggg    1440
aggatagcac aggaagatat tctgacagag aaagagagag accacattta cataacttt     1500
attacagtat attgttataa ttgttctatt ttattattag ttattgctaa tctcttactg    1560
cacctaattt ataaattaaa ccttgttatt ggtatgtatg tataggaaaa aatatagtgt    1620
atatagggct tggtactttc ttcaatttca ggcatccatt gagagtcttg gaatgtaccc    1680
actgaggata aggggggtt gctgtacata ctttgcaaat atcttctctc atcccatggg    1740
ttgtcttttc atttctttc ttttttttt tgagacggag ttttgctctt gttgcccagg    1800
ctggagtgca gtggcacaat ctcggctcac cacaatctct gcctcccggg ttcaagcgat    1860
tctcctgcct cagcctcccg agtagctggg attacaggaa tgaaccacca cgcctggcta    1920
attttttgtat ttttagtaga gatgggtttt ctccatatgg ccagcctggt ctcgaactcc    1980
cgacctcagg cgatctaccc acctcggcct cccaaagtgc tgggattaca ggtgtgagcc    2040
actgtgcctg gccgtctttt cattttcttg atggtgtcat tgaagcacaa aagttttaaa    2100
ttttgatgaa gaccaattta tctgtttttt ctttcatcac ttatgctttt ggtgtcatat    2160
```

```
ctaagaaacc attgactaat ccaaggtcac aaaagattta ttgcctatgt tttcttctaa    2220
aagttttatg attttagttc ttaaatcaag gtctatttta agtcttttgt tttgtttttt    2280
gttttttgtt ttgggacagg gtcttactct gtcacccagg ctggagtgca gaggcacatc    2340
atggctcact gcagcctcaa cctcttggcc tcaagcaatc ctcccacttc agcctcccaa    2400
ggagctggta ttatagacat gcgcaaccat gcccagctaa ttttttttgta gagatagggt    2460 ttcaccatat tgcccagact ggtctcaaac tcctaagctc cagtgatccg cccacctcag    2520
cttcccaaag ttctgggatt atagcatgag ccactgcacc cagccccaaa ttttgtatat    2580
ggtattagaa agggtccaa cttcattctt ttacatgtgg aaatccaatt gccccagcac    2640
catttgttaa aaatattttc tttcccattt aattgtccta gtgttcttgt caaaaacaat    2700
tgaacataat tgtatgggtt catttctgga ctctcaattc tattccattg ttgagcatat    2760
ttttaagggc tgttttttctc tcctgtggta actggtgacc tgtacttcct ggaagagaga    2820
tgaaaagatt cccaagccaa ctgagttacc tcacgtgggt caggtctctg tggctctctg    2880
cactggccta ttcataatga tatcctcctg caggatttga gccttctcct ttgttgtgac    2940
ggcagccgag gaggtggctg actgcccaga cagccttatc tctttcctac cttttcaaggt    3000 tattgtaaat accaaattag attgtttata cacaagaatt tagcactaaa gcactataca    3060
aatgtaagct atttatttct atttatcctt ctccttcatg aataagaccc taaaaataga    3120 agatatttt aattttact cactgggctc aaggttgcag tgtctgtatt attgcaaatt    3180
ccaaattaat gaagtctggc tcttcttata ttattcctgc aaaaggctgt gtgctacccc    3240
ccggagtgtg aatacgagtg tgggtctttc ctctttcctc tgcacccttc cttcgatgag    3300
gttttgccct ggctaggcac catgctaaac tctgagaaaa ccacagagaa caagcagacg    3360
ccatccctgc cctccagtaa catacaattt agtgatgaag ctgggatttt aacaagccat    3420
tctaataaag cgttacagtg agggaggtgc agggtgatgc ctccagcagc cctggtgtca    3480
gctgctccag gtccagggga agacttccat tatcttccaa cctgtcggaa gtggaggcgg    3540 aggctgtta ttcgtgacac agtccctaac ccagggtcta tagacattgt ggaaatgcct    3600
tggagtcaga cgggagaatg aaccagcaga agcaatgccc gccctcacct cctgaagagg    3660
gttctcagga actctttgga ggcgaggccc agtctggctg agggcctctg gatacaggtt    3720
aggcctcagg ctcttctcct ctctactcat ctctcctccc ttggcccctc cttcagaggc    3780
tgacagagcc ccactctcat ctcttcccca cccaagcctc tttccacaga aagactgctt    3840
cctcccagga gacagcagct catttgcaca cagacaccca cagccctcaa agcctggaag    3900
gccaagctgt taggacccct gagagcaggg tggctcctgg gaggagagcc caggccacca    3960
ccttgccctc cctgcccctg gcttcgatg gggctgctct gatcacaaac gtccaccaac    4020
gtagccggcc cagaagtgca cccatgtcct ctggtatcca ctggctctcc aagccaaact    4080
gggcagggag gagttgtgag ggaaaactgc aggtcaggag ggaggctggc aaagcgggcc    4140
agggccaggc ctgaccccag ctctcctctc ccggccccac tgccggccag tgtttaacaa    4200
ggccctgcct tctccctcta gtgctaggga cagccacctt cttcctctcc ccaccgcccc    4260
ctctcccctg caacacgtca tctgacaagt cagtgcgatc tcactggagg tgcatctcac    4320
aggaacgcgg ggtcacagcc tcctgcacac actccatgct gcacagcaag gtgcacgtgt    4380
cctcagagcc ccagacacat cccccactca cccagaagcc caagtgattc ccaacagccc    4440
ccagcagcct aatgggttgg ggtcttggga gcagctgtcc ctggctcctt ccctgatccc    4500
```

-continued

```
accgcccagc ctcaccccac ggttcctcca ttgccccacc tcccactgcg ccgccgggcc      4560
tctgccaggg tcaagggct tcccccctct ggcagcagac gccatggtgc cgaggtggcc       4620
tccacaaccg ccctgtgcgc caataggaca agactgtcct ccctccccca cacttgtcac      4680
tttgagggac acgtggatga gacaggaaaa cacaggggag tgtggagacc tgaggtgact      4740
tggagcaagc ctctcaacct gagcggcaat ttcttcatct gtaaaatgag ggggttgttc      4800
tcatctctga ggctttgtgt cgctctcaaa gcctgctagc ctcgggttct aggactctgt      4860
tgggatcgtg tgtgatgttt tctgctgagc gactggcagc ctgtgtcctc gggggaaag      4920 aggcaggcgc tccaaagctc ctgcgctctg tggctccccc tccctcgcag ccccaagccc      4980
caggtgtgcc ggccgccctg agcccctcca gcacctcccg gaggcgcctg caagacacct      5040
aaggtccccg cctccctcct ctcccccccg ccacacccct accccggca ggcgacgtcc       5100 ccgcccctcg accatggcct ggtgaagaag ccggccaggc ccgatcagcc ccatccccgc      5160
cgcacgagcg gcgcctgcgg acagctcctg gggccccggc cttgtcactc cggaggcggg      5220
aggctccggg gggtcgggct ggaagatcg agccggaggc cgctaggctc ccaggccccg       5280
gccgaggctg cgcggccgca cggtgggcag gctcgggtgt tccggcaaac tgccgggtcc      5340
ccatcttcaa aagagaggag gccctttctc cagcttcctc tgcgggagcc cgacccagcc      5400
ccatcccgcc accccgggc tgcacctcgg cccctcccg gccgcgccc ctgcccgggg         5460 cgggccagga acctcggccc cgccgctgg ggactttgga gcggaggagg aagcgcggcg       5520 gggcggggc gggggtgtgt cgggtttat aacccgcagg gcggccgcgg cgcaggagaa        5580
ggggcagagc                                                             5590
```

<210> SEQ ID NO 130
<211> LENGTH: 4020
<212> TYPE: DNA
<213> ORGANISM: Homo sapiens
<220> FEATURE:
<223> OTHER INFORMATION: Angiotensin I converting enzyme mRNA

<400> SEQUENCE: 130

```
gccgagcacc gcgcaccgcg tcatgggggc cgcctcgggc cgccggggc cggggctgct       60 gctgccgctg ccgctgctgt tgctgctgcc gccgcagccc gccctggcgt tggacccgg       120 gctgcagccc ggcaactttt ctgctgacga ggccggggcg cagctcttcg cgcagagcta      180
caactccagc gccgaacagg tgctgttcca gagcgtggcc gccagctggg cgcacgacac      240
caacatcacc gcggagaatg caaggcgcca ggaggaagca gccctgctca gccaggagtt      300
tgcggaggcc tggggccaga aggccaagga gctgtatgaa ccgatctggc agaacttcac      360
ggacccgcag ctgcgcagga tcatcggagc tgtgcgaacc ctgggctctg ccaacctgcc      420
cctggctaag cggcagcagt acaacgccct gctaagcaac atgagcagga tctactccac      480
cgccaaggtc tgcctcccca caagactgc cacctgctgg tccctggacc agatctcac       540 caacatcctg gcttcctcgc gaagctacgc catgctcctg tttgcctggg agggctggca      600
caacgctgcg ggcatcccgc tgaaaccgct gtacgaggat ttcactgccc tcagcaatga      660
agcctacaag caggacggct tcacagacac ggggggcctac tggcgctcct ggtacaactc      720
ccccaccttc gaggacgatc tggaacacct ctaccaacag ctagagcccc tctacctgaa      780
cctccatgcc ttcgtccgcc gcgcactgca tcgccgatac ggagacagat acatcaacct      840
caggggaccc atccctgctc atctgctggg agacatgtgg gcccagagct gggaaaacat      900
ctacgacatg gtggtgcctt tcccagacaa gcccaacctc gatgtcacca gtactatgct      960
```

-continued

```
gcagcagggc tggaacgcca cgcacatgtt ccgggtggca gaggagttct tcacctccct    1020
ggagctctcc cccatgcctc ccgagttctg ggaagggtcg atgctggaga agccggccga    1080
cgggcgggaa gtggtgtgcc acgcctcggc ttgggacttc tacaacagga aagacttcag    1140
gatcaagcag tgcacacggg tcacgatgga ccagctctcc acagtgcacc atgagatggg    1200
ccatatacag tactacctgc agtacaagga tctgcccgtc tccctgcgtc gggggggccaa    1260
ccccggcttc catgaggcca ttggggacgt gctggcgctc tcggtctcca ctcctgaaca    1320
tctgcacaaa atcggcctgc tggaccgtgt caccaatgac acggaaagtg acatcaatta    1380
cttgctaaaa atggcactgg aaaaaattgc cttcctgccc tttggctact tggtggacca    1440
gtggcgctgg ggggtcttta gtgggcgtac cccccttcc cgctacaact cgactggtg    1500
gtatcttcga accaagtatc agggatctg tcctcctgtt acccgaaacg aaacccactt    1560
tgatgctgga gctaagtttc atgttccaaa tgtgacacca tacatcaggt actttgtgag    1620
ttttgtcctg cagttccagt tccatgaagc cctgtgcaag gaggcaggct atgagggccc    1680
actgcaccag tgtgacatct accggtccac caaggcaggg gccaagctcc ggaaggtgct    1740
gcaggctggc tcctccaggc cctggcagga ggtgctgaag acatggtcg cttagatgc    1800
cctggatgcc cagccgctgc tcaagtactt ccagccagtc acccagtggc tgcaggagca    1860
gaaccagcag aacggcgagg tcctgggctg gcccgagtac cagtggcacc gccgttgcc    1920
tgacaactac ccggagggca tagacctggt gactgatgag gctgaggcca gcaagtttgt    1980
ggaggaatat gaccggacat cccaggtggt gtggaacgag tatgccgagg ccaactggaa    2040
ctacaacacc aacatcacca cagagaccag caagattctg ctgcagaaga acatgcaaat    2100
agccaaccac accctgaagt acggcaccca ggccaggaag tttgatgtga accagttgca    2160
gaacaccact atcaagcgga tcataaagaa ggttcaggac ctagaacggg cagcgctgcc    2220
tgcccaggag ctggaggagt acaacaagat cctgttggat atggaaacca cctacagcgt    2280
ggccactgtg tgccaccgga atggcagctg cctgcagctc gagccagatc tgacgaatgt    2340
gatggccaca tcccggaaat atgaagacct gttatgggca tgggagggct ggcgagacaa    2400
ggcgggaga gccatcctcc agttttaccc gaaatacgtg gaactcatca accaggctgc    2460
ccggctcaat ggctatgtag atgcagggga ctcgtggagg tctatgtacg agacaccatc    2520
cctggagcaa gacctggagc ggctcttcca ggagctgcag ccactctacc tcaacctgca    2580
tgcctacgtg cgccgggccc tgcaccgtca ctacgggcc cagcacatca acctggaggg    2640
gcccattcct gctcacctgc tgggaacat gtgggcgcag acctggtcca acatctatga    2700
cttggtggtg cccttcccct cagccccctc gatggacacc acagaggcta tgctaaagca    2760
gggctggacg cccaggagga tgtttaagga ggctgatgat tcttcacct ccctgggct    2820
gctgcccgtg cctcctgagt ctggaacaa gtcgatgctg gagaagccaa ccgacgggcg    2880
ggaggtggtc tgccacgcct cggcctggga cttctacaac ggcaaggact tccggatcaa    2940
gcagtgcacc accgtgaact tggaggacct ggtggtggcc caccgaaa tgggccacat    3000
ccagtatttc atgcagtaca aagcttacc tgtggccttg agggagggtg ccaaccccgg    3060
cttccatgag gccattgggg acgtgctagc cctctcagtg tctacgccca gcacctgca    3120
cagtctcaac ctgctgagca gtgagggtgg cagcgacgag catgacatca actttctgat    3180
gaagatggcc cttgacaaga tcgcctttat ccccttcagc tacctcgtcg atcagtggcg    3240
ctggagggta tttgatggaa gcatcaccaa ggagaactat aaccaggagt ggtggagcct    3300
```

-continued

```
caggctgaag taccagggcc tctgccccc agtgcccagg actcaaggtg actttgaccc      3360
aggggccaag ttccacattc cttctagcgt gccttacatc aggtactttg tcagcttcat      3420
catccagttc cagttccacg aggcactgtg ccaggcagct ggccacacgg gcccctgca       3480 caagtgtgac atctaccagt ccaaggaggc cgggcagcgc ctggcgaccg ccatgaagct      3540
gggcttcagt aggccgtggc cggaagccat gcagctgatc acgggccagc caacatgag      3600 cgcctcggcc atgttgagct acttcaagcc gctgctggac tggctccgca cggagaacga     3660
gctgcatggg gagaagctgg gctggccgca gtacaactgg acgccgaact ccgctcgctc     3720
agaagggccc ctcccagaca gcggccgcgt cagcttcctg ggcctggacc tggatgcgca     3780
gcaggcccgc gtgggccagt ggctgctgct cttcctgggc atcgccctgc tggtagccac     3840
cctgggcctc agccagcggc tcttcagcat ccgccaccgc agcctccacc ggcactccca    3900
cgggccccag ttcggctccg aggtggagct gagacactcc tgaggtgacc cggctgggtc    3960
ggccctgccc aagggcctcc caccagagac tgggatggga acactggtgg gcagctgagg   4020
```

<210> SEQ ID NO 131
<211> LENGTH: 2720
<212> TYPE: DNA
<213> ORGANISM: Homo sapiens
<220> FEATURE:
<223> OTHER INFORMATION: Angiotensin II type I receptor, promoter region

<400> SEQUENCE: 131

```
aagcttgctg gggttttgat agagattttg tttaacctgt agatcatttg aagattaatg       60
ccattgtaac gatattaaat ctttcaatcc aagaacatgg aatgtcattc catttattta      120
ggtctacctt atttcaacaa ttcttttttgt ttgttttcag actacaagtt ttagatcctt     180
ttgttaaatt tatttcttag ggttttttttt gttttgtttt gttttgttgg ttggttggtt    240
tgttttgaga tggagtctca ctctgtcacc caggctggag tgcagtggca caatctcagc    300
tcacagcaac ctctacctcc tgggttcaag cgattattct gcctcagcct cctcctcctg   360
agtagctgga actacaggca tgcaccacca cgcctggcct ttttttttttt tttttcttt    420 gcatttttag tagagacagg gtttcacgat gttggccagc ctggtctcga atccctgacc    480
ttgtgattca cccacctcgg cctcccaaag tgctgagatt acaggagtga gccactacac    540
caggtcattt cttgatattt ttactctttt gatctatagt aagtaaaatt gtttttatct    600
ttgaattttt aaatttttaa cacagttcaa atcagtgtgt ctgatttcat ctccttctct   660
aacaaaccag ggtgccagaa ctgcttcagt ttctctgcct tctctttgtc tatgatgact   720
aatgtatgaa ggtatctgct gcatcaaact ttaaacttca cattatcctt atttctcttg   780
accttgacag atctggcatc ttttcacctg gtcgtaagca gaaagtcctt gatctcctta   840 acttttttgag gcatggcagc atgtgaggca gggagaggac acagacccac acagcaagtg   900
gtgagaagcc aacagtggaa ttgttttctt aattccattt gttgattgtt tattgctagt    960
gtatagaaat acaactgatt tttgtatatt gatcttgtat tctaaaaact tgctcaactt  1020
gtttcttagt tctaatagtt aattaattga ttccttaggg cttttttaata caagatcatg  1080 tcatctacaa atagaaattg tttttactttc tttctaatct ggatgccatt tatctttttt   1140
tcttgtccaa ttgccctcac tagaaccttt agtacaaagt taaatagaaa tgggaagact   1200
agacattttg tcttgttcct gatcttagac ataaaaacgt tgtcttccgt tattatgtgt   1260
gatattagtt aagttaagtt tttcataaat aaacttcaca gtttgaggaa gttcctattc   1320
ctaatttgtt gagtgttagc atgaaaaagt gttgaatttt gtccaagagt tttaaaaat    1380
```

```
ttttttagac aatcatgtag gctttgtcca ttttttactt ctttaaattt attttatttg    1440
atacacaata gatgtacact ttttaggtac atgcaataat ttaatgcccc tcactataaa    1500
ttcggagctg cctcctcgcc gatgattcca gcgcctgaca gccaggaccc caggcagcag    1560
cgagtgacag gacttttag gtacatgcaa taatttaatg cattcatata aagatcaaat    1620
cagtgcaatt ggcatatcca tcaccttaaa tatttgtctt tttcttcatg ctagaaacat    1680
tcaagttatt ttctcctagc tactctgaaa tatacaatag attactgtaa actacagtca    1740
ccctactcac ctatctaaca ttaattgatt tttggtaaac taatctaatc ttgctttctg    1800
gcatcaacct cacttgacca tggtgtatag tccctttcat atgttattgg attcaatttg    1860
cctacatttt gttgagaatt tttatctata ctcttaagaa atattgatct gtagtctcgt    1920
gatgtcttta tctggttttg ttatcagggt gatactggcc tcatagcatg agttgggaga    1980
tcatccttac tcttctattt tttggaagag tttgtgaaga attgatatta tttcttcttt    2040
aaatatttat tgggttttta aaatacattt ttaaaatgca acttgggtag catgtccaat    2100
aggaacaaat gagtgtccac ccttgaattt cataaccctc ggaattaatc catgtaatct    2160
atgatccaca actgtattac caaagttcga gttactcata ggaaagagaa agaagttctc    2220
taattcgtcc ttaaaagttt tccaagttca gaaaaaaaaa atgttgaaga acacgaactc    2280
ccgcaggaaa tgatactcct gtaccccag ctcgctctcc ctcacgaccc ctcgctaggc    2340
ggggttcggg accaggtgaa cgctgatctg atagttgaca cgggacgact gtggcatcat    2400
ccttgctgcc gtcaatatcc cgagagggag gaggttgggc cgggagggtc tccggggcgg    2460
ggcggaggag gagggaatgc aaaacagagc ctcgtcccg gaacccaaga agcagcaacg    2520
cccctcacta taaattcgga gctgcctcct cgccaatgat tccagcgcct gacagccagg    2580
accccaggca gcagcgagtg acaggacgtc tggaccggcg cgccgctagc agctctgccg    2640
ggccgcggcg gtgatcgatg gggagcggct ggagcggacc cagcgagtga gggcgcacag    2700
ccgggacgcc gaggcggcgg                                                 2720
```

<210> SEQ ID NO 132
<211> LENGTH: 480
<212> TYPE: DNA
<213> ORGANISM: Homo sapiens
<220> FEATURE:
<223> OTHER INFORMATION: Type I Angiotensin II receptor isoform, exon 3

<400> SEQUENCE: 132

```
gaattctcag agctggcgaa acagtctggt ccaagcagcc tctcagcagt gcctttcagc     60
ctcccctctc tgagtctttc caccccttgc tggtacttta gtttcttcca cttctagcac    120
cacgtgtagt ttcccaattt ctcttaccca aatttgctca cagggaaaaa ataaattaa     180 attagccatt tacaccacag tgtgaactta ataacaccaa caaagttcc aaagctctag     240 ggtctcatag cacctccaga tccatgatct cattcggtgt ttccaacaat gttttgcacc    300
aaactggaca catgcttgct acttcatcat cctcatcgtg aacattatta ttattatcat    360
cattttccag atgaagaaaa tgaatcacaa gtcaactgac agtccaaagg ctccacagct    420
cagaggaggt aaatcatgtg cttaattcag aactttggc tcccatcact atgctcttcc     480
```

<210> SEQ ID NO 133
<211> LENGTH: 2268
<212> TYPE: DNA
<213> ORGANISM: Homo sapiens
<220> FEATURE:

<223> OTHER INFORMATION: Type I angiotensin II receptor, exon 5

<400> SEQUENCE: 133

```
accccaggca gcagcgagtg acaggacgtc tggaccggcg cgccgctagc agctctgccg     60
ggccgcggcg gtgatcgatg gggagcggct ggagcggacc cagcgagtga gggcgcacag    120
ccgggacgcc gaggcggcg gcgggagacc cgcaccagcg cagccggccc tcggcgggac     180
gtgacgcagc gcccggggcg cgggtttgat atttgacaaa ttgatctaaa atggctgggt    240
ttttatctga ataactcact gatgccatcc cagaaagtcg gcaccaggtg tatttgatat    300
agtgtttgca acaaattcga cccaggtgat caaaatgatt ctcaactctt ctactgaaga    360
tggtattaaa agaatccaag atgattgtcc caaagctgga aggcataatt acatatttgt    420
catgattcct actttataca gtatcatctt tgtggtggga atatttggaa acagcttggt    480
ggtgatagtc atttactttt atatgaagct gaagactgtg ccagtgtttt tcttttgaa     540
tttagcactg gctgacttat gcttttact gactttgcca ctatgggctg tctacacagc     600
tatggaatac cgctggccct ttggcaatta cctatgtaag attgcttcag ccagcgtcag    660
tttcaacctg tacgctagtg tgtttctact cacgtgtctc agcattgatc gatacctggc    720
tattgttcac ccaatgaagt cccgccttcg acgcacaatg cttgtagcca agtcacctg     780
catcatcatt tggctgctgg caggcttggc cagtttgcca gctataatcc atcgaaatgt    840
atttttcatt gagaacacca atattacagt ttgtgctttc cattatgagt cccaaaattc    900
aaccccttccg atagggctgg gcctgaccaa aaatatactg ggtttcctgt tccttttct    960
gatcattctt acaagttata ctcttatttg gaaggcccta agaaggcttt atgaaattca   1020
gaagaacaaa ccaagaaatg atgatatttt taagataatt atggcaattg tgcttttctt   1080
tttcttttcc tggattcccc accaaatatt cacttttctg gatgtattga ttcaactagg   1140
catcatacgt gactgtagaa ttgcagatat tgtggacacg ccatgccta tcaccatttg    1200
tatagcttat tttaacaatt gcctgaatcc tcttttttat ggctttctgg ggaaaaaatt   1260
taaaagatat tttctccagc ttctaaaata tattccccca aaagccaaat cccactcaaa   1320
cctttcaaca aaaatgagca cgctttccta ccgcccctca gataatgtaa gctcatccac   1380
caagaagcct gcaccatgtt ttgaggttga gtgacatgtt cgaaacctgt ccataaagta   1440
attttgtgaa agaaggagca agagaacatt cctctgcagc acttcactac caaatgagca   1500
ttagctactt ttcagaattg aaggagaaaa tgcattatgt ggactgaacc gacttttcta   1560
aagctctgaa caaagctttt ctttcctttt tgcaacaaga caaagcaaag ccacattttg   1620
cattagacag atgacggctg ctcgaagaac aatgtcagaa actcgatgaa tgtgttgatt   1680
tgagaaattt tactgacaga aatgcaatct ccctagcctg cttttgtcct gttatttttt   1740
atttccacat aaaggtattt agaatatatt aaatcgttag aggagcaaca ggagatgaga   1800
gttccagatt gttctgtcca gtttccaaag ggcagtaaag ttttcgtgcc ggttttcagc   1860
tattagcaac tgtgctacac ttgcacctgg tactgcacat tttgtacaaa gatatgctaa   1920
gcagtagtcg tcaagttgca gatcttttg tgaaattcaa cctgtgtctt ataggtttac    1980
actgccaaaa caatgcccgt aagatggctt atttgtataa tggtgttact aaagtcacat   2040
ataaaagtta aactacttgt aaaggtgctg cactggtccc aagtagtagt gtcctcctag   2100
```

-continued

```
tatattagtt tgatttaata tctgagaagt gtatatagtt tgtggtaaaa agattatata    2160
tcataaagta tgccttcctg tttaaaaaaa gtatatattc tacacatata tatatatgta    2220
tatctatatc tctaaactgc tgttaattga ttaaaatctg gcaaagtt                 2268
```